United States Patent
Inokuchi et al.

(10) Patent No.: US 8,293,366 B2
(45) Date of Patent: *Oct. 23, 2012

(54) COSMETIC

(75) Inventors: Yoshinori Inokuchi, Annaka (JP); Ryuichi Inaba, Ichikawa (JP); Ryuji Horiguchi, Takasaki (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 192 days.

This patent is subject to a terminal disclaimer.

(21) Appl. No.: 12/693,877

(22) Filed: Jan. 26, 2010

(65) Prior Publication Data
US 2011/0117146 A1 May 19, 2011

(30) Foreign Application Priority Data
Nov. 18, 2009 (JP) ................................. 2009-263413

(51) Int. Cl.
*B32B 5/16* (2006.01)
*B32B 27/28* (2006.01)
*B05D 7/00* (2006.01)

(52) U.S. Cl. ......... 428/403; 428/406; 428/407; 427/212

(58) Field of Classification Search ........................ None
See application file for complete search history.

(56) References Cited

U.S. PATENT DOCUMENTS

| 4,970,252 | A | | 11/1990 | Sakuta et al. | |
|---|---|---|---|---|---|
| 5,538,793 | A | * | 7/1996 | Inokuchi et al. | 428/407 |
| 5,773,134 | A | * | 6/1998 | Inokuchi et al. | 428/220 |
| 8,133,586 | B2 | * | 3/2012 | Inokuchi et al. | 428/403 |
| 2010/0112023 | A1 | * | 5/2010 | Inokuchi et al. | 424/401 |
| 2010/0112074 | A1 | * | 5/2010 | Inokuchi et al. | 424/497 |

FOREIGN PATENT DOCUMENTS

| EP | 0 661 334 A1 | * | 7/1995 |
|---|---|---|---|
| EP | 0 958 805 | * | 11/1999 |
| EP | 1 582 203 A1 | * | 10/2005 |

* cited by examiner

*Primary Examiner* — Richard Schnizer
*Assistant Examiner* — Alma Pipic
(74) *Attorney, Agent, or Firm* — Birch, Stewart, Kolasch & Birch, LLP

(57) ABSTRACT

Provided is a cosmetic including silicone microparticles, in which the silicone microparticles include 100 parts by mass of silicone elastomer spherical microparticles having a volume average particle diameter within a range from 0.1 to 100 µm, and 0.5 to 25 parts by mass of a polyorganosilsesquioxane that coats the surface of the silicone elastomer spherical microparticles, and the silicone elastomer is capable of absorbing not less than 200 parts by mass of a polymethylsiloxane having a viscosity at 25° C. of not more than 10 mm$^2$/s per 100 parts by mass of the silicone elastomer. Even if containing a silicone oil, the cosmetic exhibits favorable feelings upon use, with no spreading difficulties, stickiness, greasiness, or oily film feeling or the like.

5 Claims, No Drawings

COSMETIC

BACKGROUND OF THE INVENTION

1. Field of the Invention

The present invention relates to a cosmetic.

2. Description of the Prior Art

Cosmetics containing silicone oils have conventionally been used for the purposes of obtaining a protection effect, softening effect, smoothing effect and moisturizing effect and the like on the skin. However, these types of cosmetics suffer from drawbacks, including spreading difficulties, stickiness, greasiness and an oily film feeling. For example, Patent Document 1 proposes a cosmetic containing a composition composed of a low-viscosity silicone oil and a cross-linked organopolysiloxane obtained by performing an addition polymerization between an organohydrogenpolysiloxane and an organopolysiloxane. This cosmetic is able to address some of the drawbacks listed above, but there are problems in that, the addressing is not satisfactory, and if the silicone oil volatilizes during application to the skin, then the cosmetic becomes difficult to spread and the silkiness then deteriorates.

On the other hand, silicone particles have been used conventionally to impart cosmetics with feelings during use, such as a feeling of silkiness or smoothness, and extensibility. In particular, silicone microparticles comprising spherical microparticles of a silicone rubber coated with a polyorganosilsesquioxane (see Patent Document 2) have a soft feel, are non-cohesive, and exhibit excellent dispersibility, and are therefore used in a wide variety of cosmetics. However, no existing documents make mention of silicone microparticles that achieve the effect of addressing the drawbacks mentioned above associated with cosmetics containing an added silicone oil.

Patent Document 1: U.S. Pat. No. 4,970,252

Patent Document 2: U.S. Pat. No. 5,538,793

SUMMARY OF THE INVENTION

The present invention has an object of providing a cosmetic which, even if containing a silicone oil, exhibits favorable feelings upon use, with no spreading difficulties, stickiness, greasiness, or oily film feeling or the like.

As a result of intensive investigation aimed at achieving the above object, the inventors of the present invention discovered that the above object could be achieved by using the cosmetic described below, and the inventors were therefore able to complete the present invention.

In other words, the present invention provides:

a cosmetic comprising silicone microparticles, wherein the silicone microparticles comprise 100 parts by mass of silicone elastomer spherical microparticles having a volume average particle diameter within a range from 0.1 to 100 μm, and 0.5 to 25 parts by mass of a polyorganosilsesquioxane that coats the surface of the silicone elastomer spherical microparticles, and the silicone elastomer is capable of absorbing not less than 200 parts by mass of a polymethylsiloxane having a viscosity at 25° C. of not more than 10 mm$^2$/s per 100 parts by mass of the silicone elastomer.

Even if containing a silicone oil, the cosmetic of the present invention exhibits favorable feelings upon use, with no spreading difficulties, stickiness, greasiness, oily film feeling, or the like.

DETAILED DESCRIPTION OF THE PREFERRED EMBODIMENTS

A more detailed description of the present invention is provided below, where viscosity values refer to kinetic viscosity values measured at 25° C. using an Ostwald viscometer.

The cosmetic of the present invention is characterized by comprising the silicone microparticles described above. The cosmetic is applicable to a variety of cosmetics, but is particularly preferable for cosmetics applied externally to the skin such as skincare cosmetics, makeup cosmetics, antiperspirants and ultraviolet protection cosmetics, and cosmetics applied externally to the hair such as hair cosmetics. Examples of the skincare cosmetics include cosmetic washes, lotions, creams, cleansing materials, packs, oil liquids, massage formulations, beauty lotions, beauty oils, cleansing agents, deodorants, hand creams, lip creams and wrinkle concealers. Examples of the makeup cosmetics include makeup foundations, concealers, whitening powders, powder foundations, liquid foundations, cream foundations, oily foundations, blushers, eye colorants, eye shadows, mascaras, eye liners, eyebrow materials and lipsticks. Examples of the antiperspirants include roll-on type, cream type, solution type and stick type antiperspirants. Examples of the ultraviolet protection cosmetics include sunblock oils, sunblock lotions and sunblock creams. Examples of the hair cosmetics include shampoos, rinses, treatments and setting agents.

The form of the cosmetic of the present invention may be any of a powder, oily liquid, water-in-oil emulsion, oil-in-water emulsion, non-aqueous emulsion, or a multi-emulsion of a W/O/W type, O/W/O type, or the like. Further, the physical state of the cosmetic of the present invention may be selected from a variety of physical states such as a liquid, emulsion, cream, solid, paste, gel, powder, pressed state, multilayered state, mousse, spray, stick, pencil, or the like.

[Silicone Microparticles]

As mentioned above, the silicone microparticles used in the present invention comprise 100 parts by mass of silicone elastomer spherical microparticles having a volume average particle diameter within a range from 0.1 to 100 μm, and 0.5 to 25 parts by mass of a polyorganosilsesquioxane that coats the surface of the silicone elastomer spherical microparticles, where the silicone elastomer is capable of absorbing not less than 200 parts by mass of a polymethylsiloxane having a viscosity at 25° C. of not more than 10 mm$^2$/s per 100 parts by mass of the silicone elastomer. The silicone microparticles may employ either a single type of microparticle or a combination of two or more different types. In the cosmetic of the present invention, there are no particular restrictions on the blend amount or the combination of the silicone microparticles. It is preferable that the blend amount of the silicone microparticles is appropriately selected within a range from 0.1 to 95.0% by mass of the entire cosmetic in accordance with the form, physical state, and the like of the product cosmetic.

(Silicone Elastomer Spherical Microparticles)

In the silicone microparticles described above, the silicone elastomer spherical microparticles that are surface-coated with a polyorganosilsesquioxane have a volume average particle diameter that is within a range from 0.1 to 100 μm, and preferably from 1 to 40 μm. If this volume average particle diameter is less than 0.1 μm, then the resulting silicone microparticles may be less likely to exhibit the silkiness and smoothness. If the volume average particle diameter exceeds 100 μm, then the silkiness and smoothness of the resulting silicone microparticles tends to deteriorate, and a feeling of grittiness may also develop. The volume average particle diameter is measured using a Coulter counter method. Further, in this description, the teen "spherical" means that microparticles have not only a perfectly spherical shape but also deformed spherical shapes in which (length of longest axis)/(length of shortest axis) (the aspect ratio) is typically within a range from 1 to 4, preferably from 1 to 2, more preferably from 1 to 1.6, and still more preferably from 1 to 1.4, on average. The shapes of the microparticles can be confirmed by inspecting the microparticles under an optical microscope, an electron microscope, and the like.

The silicone elastomer that constitutes the silicone elastomer spherical microparticles preferably exhibits no stickiness, and preferably has a rubber hardness, measured using a type A durometer prescribed in JIS K 6253, that is within a range from 5 to 90, and more preferably from 10 to 80. Provided the rubber hardness is within a range from 5 to 90, cohesion of the obtained silicone microparticles can be adequately suppressed, and microparticles having excellent levels of flowability and dispersibility, and superior feelings of silkiness, smoothness and softness can be obtained.

The silicone elastomer is capable of absorbing not less than 200 parts by mass of a polymethylsiloxane having a viscosity at 25° C. of not more than 10 mm$^2$/s per 100 parts by mass of the silicone elastomer. If the amount of the polymethylsiloxane absorbed is less than 200 parts by mass, then the effect of the obtained silicone microparticles in suppressing the greasiness, stickiness, and oily film feeling of cosmetic materials containing such polymethylsiloxanes tends to weaken. The greater the amount of polymethylsiloxane absorbed the better, and therefore there are no particular limitations on the upper limit for the absorption amount, although for practical reasons, the absorption amount may be, for example, not more than 1,000 parts by mass, and particularly not more than 500 parts by mass.

The structure of the polymethylsiloxane may be a linear, cyclic or branched structure. Examples of the polymethylsiloxane include dimethylpolysiloxanes represented by the formula: $(CH_3)_3SiO[(CH_3)_2SiO]_nSi(CH_3)_3$ (wherein n is a positive number that satisfies $1 \leq n \leq 15$), decamethylcyclopentasiloxane, and the methylsiloxane represented by the formula: $[(CH_3)_3SiO]_3SiCH_3$.

The silicone elastomer is preferably a cured product of a liquid silicone composition comprising:

(A)

(A1) an organopolysiloxane represented by an average composition formula (1) shown below:

$$R^1_a R^2_b SiO_{(4-a-b)/2} \tag{1}$$

(wherein $R^1$ represents an unsubstituted or substituted monovalent hydrocarbon group of 1 to 30 carbon atoms excluding aliphatic unsaturated groups, $R^2$ represents a monovalent olefinic unsaturated group of 2 to 6 carbon atoms, and a and b are positive numbers that satisfy $0<a<3$, $0<b\leq3$, and $0.1\leq a+b\leq3$, provided that the proportion of monovalent hydrocarbon groups of 6 to 30 carbon atoms is less than 5 mol % of all the $R^1$ groups),
in which not less than 90 mol % of all the siloxane units other than the siloxane units at the molecular terminals are dimethylsiloxane units represented by a formula: $-(CH_3)_2SiO-$, and having a molecular weight of not less than 5,000, having two monovalent olefinic unsaturated groups within each molecule, and having a monovalent olefinic unsaturated group content of not more than 0.04 mol/100 g, (A2) an organopolysiloxane represented by the above average composition formula (1), in which not less than 90 mol % of all the siloxane units other than the siloxane units at the molecular terminals are dimethylsiloxane units represented by a formula: $-(CH_3)_2SiO-$, and having a molecular weight of not less than 5,000, having at least three monovalent olefinic unsaturated groups within each molecule, and having a monovalent olefinic unsaturated group content of not more than 0.06 mol/100 g, or
a combination of component (A1) and component (A2), (B)

(B1) an organohydrogenpolysiloxane represented by an average composition formula (2) shown below:

$$R^3_c H_d SiO_{(4-c-d)/2} \tag{2}$$

(wherein $R^3$ represents an unsubstituted or substituted monovalent hydrocarbon group of 1 to 30 carbon atoms excluding aliphatic unsaturated groups, and c and d are positive numbers that satisfy $0<c<3$, $0<d\leq3$, and $0.1\leq c+d\leq3$, provided that the proportion of monovalent hydrocarbon groups of 6 to 30 carbon atoms is less than 5 mol % of all the $R^3$ groups),
in which not less than 90 mol % of all the siloxane units other than the siloxane units at the molecular terminals are dimethylsiloxane units represented by a formula: $-(CH_3)_2SiO-$, and having a molecular weight of not less than 5,000, having two hydrogen atoms bonded to silicon atoms within each molecule, and having a silicon atom-bonded hydrogen atom content of not more than 0.04 mol/100 g, (B2) an organohydrogenpolysiloxane represented by the above average composition formula (2), in which not less than 90 mol % of all the siloxane units other than the siloxane units at the molecular terminals are dimethylsiloxane units represented by a formula: $-(CH_3)_2SiO-$, and having a molecular weight of not less than 5,000, having at least three hydrogen atoms bonded to silicon atoms within each molecule, and having a silicon atom-bonded hydrogen atom content of not more than 0.06 mol/100 g, or
a combination of component (B1) and component (B2),
in an amount that yields from 0.5 to 2 hydrogen atoms bonded to silicon atoms within component (B) per monovalent olefinic unsaturated group within component (A), and (C) A Platinum Group Metal-Based Catalyst, provided that when component (A) is component (A1), component (B) is either component (B2) or a combination of component (B1) and component (B2).

Component (A)

The component (A) is an organopolysiloxane comprising a monovalent olefinic unsaturated group within each molecule, and may be either the component (A1), the component (A2), or a combination of the component (A1) and the component (A2). The component (A1) and the component (A2) may each employ either a single compound or a combination of two or more compounds.

Preferably, a and b are positive numbers that satisfy $0<a\leq2.295$, $0.005\leq b\leq2.3$, and $0.5\leq a+b\leq2.3$.

The number of carbon atoms within $R^1$ is typically within a range from 1 to 30, and is preferably from 1 to 20, and more preferably from 1 to 6. Specific examples of $R^1$ include alkyl groups such as a methyl group, ethyl group, propyl group, butyl group, pentyl group, hexyl group, heptyl group, octyl group, decyl group, undecyl group, dodecyl group, tetradecyl group, pentadecyl group, hexadecyl group, heptadecyl group, octadecyl group, nonadecyl group, icosyl group, henicosyl group, docosyl group, tricosyl group, tetracosyl group or triacontyl group; aryl groups such as a phenyl group, tolyl group or naphthyl group; aralkyl groups such as a benzyl group or phenethyl group; cycloalkyl groups such as a cyclopentyl group, cyclohexyl group or cycloheptyl group; and monovalent hydrocarbon groups in which some or all of the hydrogen atoms bonded to carbon atoms in any of the above groups have been substituted with either one or both of an atom such as a halogen atom (such as a fluorine atom, chlorine atom, bromine atom or iodine atom) and a substituent such as an acryloyloxy group, methacryloyloxy group, epoxy group, glycidoxy group or carboxyl group.

The proportion of monovalent hydrocarbon groups of 6 to 30 carbon atoms within all of the $R^1$ groups is typically less than 5 mol % (at least 0 mol % and less than 5 mol %), and is preferably not more than 2 mol % (from 0 to 2 mol %). If this proportion is 5 mol % or greater, then the amount of the aforementioned polymethylsiloxane absorbed by the obtained silicone microparticles tends to decrease.

The number of carbon atoms with $R^2$ is typically from 2 to 6. Specific examples of $R^2$ include a vinyl group, allyl group, propenyl group, butenyl group, pentenyl group or hexenyl group. From an industrial perspective, a vinyl group is preferred.

In the organopolysiloxane of the component (A), the amount of dimethylsiloxane units represented by the formula —$(CH_3)_2SiO$— represents not less than 90 mol % (90 to 100 mol %), and preferably not less than 95 mol % (95 to 100 mol %) of all the siloxane units other than the siloxane units at the molecular terminals (hereafter, also referred to as "all the non-terminal siloxane units"). If this amount is less than 90 mol %, then the amount of the aforementioned polymethylsiloxane absorbed by the obtained silicone microparticles tends to decrease.

In the organopolysiloxane of the component (A), of the siloxane units other than the siloxane units at the molecular terminals (hereafter, these siloxane units may also be referred to as "the non-terminal siloxane units"), examples of the siloxane units other than the dimethylsiloxane units represented by the formula —$(CH_3)_2SiO$— include $R^{11}_2SiO_{2/2}$ units, $R^1R^2SiO_{2/2}$ units, $R^2_2SiO_{2/2}$ units, $R^1SiO_{3/2}$ units, $R^2SiO_{3/2}$ units and $SiO_{4/2}$ units (wherein $R^{11}$ represents an unsubstituted or substituted monovalent hydrocarbon group of 2 to 30 carbon atoms, preferably 2 to 20 carbon atoms, and more preferably 2 to 6 carbon atoms, excluding aliphatic unsaturated groups, and $R^1$ and $R^2$ are as defined above).

Specific examples of $R^{11}$ include the same monovalent hydrocarbon groups as those exemplified above for $R^1$ excluding the unsubstituted methyl group and substituted methyl groups.

In the organopolysiloxane of the component (A), the amount of the non-terminal siloxane units that are other than dimethylsiloxane units represented by the formula —$(CH_3)_2SiO$— is typically not more than 10 mol % (0 to 10 mol %), and preferably not more than 5 mol % (0 to 5 mol %) of all the non-terminal siloxane units. If this amount exceeds 10 mol %, then the amount of the aforementioned polymethylsiloxane absorbed by the obtained silicone microparticles tends to decrease. In those cases where the amount of at least one type of unit amongst $R^1SiO_{3/2}$ units, $R^2SiO_{3/2}$ units (wherein $R^1$ and $R^2$ are as defined above) and $SiO_{4/2}$ units is large, the resulting silicone microparticles tend to be particularly prone to a reduction in the amount of polymethylsiloxane absorbed, and therefore the combined amount of these siloxane units is preferably not more than 2 mol % (0 to 2 mol %) of all the non-terminal siloxane units.

In the organopolysiloxane of the component (A), examples of the siloxane units at the molecular terminals include $R^1_3SiO_{1/2}$ units, $R^1_2R^2SiO_{1/2}$ units, $R^1R^2_2SiO_{1/2}$ units, and $R^2_3SiO_{1/2}$ units (wherein $R^1$ and $R^2$ are as defined above).

The molecular weight of the organopolysiloxane of the component (A) is typically not less than 5,000, and is preferably 8,000 or greater. If this molecular weight is less than 5,000, then the amount of the aforementioned polymethylsiloxane absorbed by the obtained silicone microparticles tends to decrease. On the other hand, the molecular weight is preferably not more than 200,000. Provided the molecular weight is not more than 200,000, the viscosity of the component (A) can be prevented from becoming overly high, and the production method described below can be used to easily generate silicone microparticles having a narrow particle size distribution.

In the organopolysiloxane of the component (A1), the monovalent olefinic unsaturated group content is typically not more than 0.04 mol/100 g, and is preferably not more than 0.02 mol/100 g. Further, in the organopolysiloxane of the component (A2), the monovalent olefinic unsaturated group content is typically not more than 0.06 mol/100 g, and is preferably not more than 0.04 mol/100 g. In those cases where the monovalent olefinic unsaturated group content within the component (A1) exceeds 0.04 mol/100 g, or the monovalent olefinic unsaturated group content within the component (A2) exceeds 0.06 mol/100 g, or both these conditions apply, the amount of the aforementioned polymethylsiloxane absorbed by the obtained silicone microparticles tends to decrease. Although there are no particular restrictions on the lower limit for the monovalent olefinic unsaturated group content, for practical reasons, the monovalent olefinic unsaturated group content in the component (A1) may be, for example, 0.001 mol/100 g or greater, and the monovalent olefinic unsaturated group content in the component (A2) may be, for example, 0.0015 mol/100 g or greater.

Component (B)

The component (B) is an organohydrogenpolysiloxane comprising hydrogen atoms bonded to silicon atoms (hereafter also referred to as "SiH groups") within each molecule. The component (B) may be either the component (B1), the component (B2), or a combination of the component (B1) and the component (B2). The component (B1) and the component (B2) may each employ either a single compound or a combination of two or more compounds.

Preferably, c and d are positive numbers that satisfy $0<c \leq 2.295$, $0.005 \leq d \leq 2.3$, and $0.5 \leq c+d \leq 2.3$.

The number of carbon atoms within $R^3$ is typically within a range from 1 to 30, and is preferably from 1 to 20, and more preferably from 1 to 6. Specific examples of $R^3$ include the same groups as those exemplified above for $R^1$.

The proportion of monovalent hydrocarbon groups of 6 to 30 carbon atoms within all of the $R^3$ groups is typically less than 5 mol % (at least 0 mol % and less than 5 mol %), and is preferably not more than 2 mol % (from 0 to 2 mol %). If this proportion is 5 mol % or greater, then the amount of the aforementioned polymethylsiloxane absorbed by the obtained silicone microparticles tends to decrease.

In the organohydrogenpolysiloxane of the component (B), the amount of dimethylsiloxane units represented by the formula —$(CH_3)_2SiO$— represents not less than 90 mol % (90 to 100 mol %), and preferably not less than 95 mol % (95 to 100 mol %) of all the siloxane units other than the siloxane units at the molecular terminals. If this amount is less than 90 mol %, then the amount of the aforementioned polymethylsiloxane absorbed by the obtained silicone microparticles tends to decrease.

In the organohydrogenpolysiloxane of the component (B), examples of the non-terminal siloxane units other than the dimethylsiloxane units represented by the formula —$(CH_3)_2SiO$— include $R^{31}_2SiO_{2/2}$ units, $R^3HSiO_{2/2}$ units, $H_2SiO_{2/2}$ units, $R^3SiO_{3/2}$ units, $HSiO_{3/2}$ units and $SiO_{4/2}$ units (wherein $R^{31}$ represents an unsubstituted or substituted monovalent hydrocarbon group of 2 to 30 carbon atoms, preferably 2 to 20 carbon atoms, and more preferably 2 to 6 carbon atoms, excluding aliphatic unsaturated groups, and $R^3$ is as defined above).

Specific examples of $R^{31}$ include the same monovalent hydrocarbon groups as those exemplified above for $R^1$ excluding the unsubstituted methyl group and substituted methyl groups.

In the organohydrogenpolysiloxane of the component (B), the amount of the non-terminal siloxane units that are other than dimethylsiloxane units represented by the formula —$(CH_3)_2SiO$— is typically not more than 10 mol % (0 to 10 mol %), and preferably not more than 5 mol % (0 to 5 mol %) of all the non-terminal siloxane units. If this amount exceeds 10 mol %, then the amount of the aforementioned polymethylsiloxane absorbed by the obtained silicone microparticles tends to decrease. In those cases where the amount of at least one type of unit amongst $R^3SiO_{3/2}$ units, $HSiO_{3/2}$ units (wherein $R^3$ is as defined above) and $SiO_{4/2}$ units is large, the resulting silicone microparticles tend to be particularly prone to a reduction in the amount of polymethylsiloxane absorbed, and therefore the combined amount of these siloxane units is preferably not more than 2 mol % (0 to 2 mol %) of all the non-terminal siloxane units.

In the organohydrogenpolysiloxane of the component (B), examples of the siloxane units at the molecular terminals include $R^3{}_3SiO_{1/2}$ units, $R^3{}_2HSiO_{1/2}$ units, $R^3H_2SiO_{1/2}$ units, and $H_3SiO_{1/2}$ units (wherein $R^3$ is as defined above).

The molecular weight of the organohydrogenpolysiloxane of the component (B) is typically not less than 5,000, and is preferably 8,000 or greater. If this molecular weight is less than 5,000, then the amount of the aforementioned polymethylsiloxane absorbed by the obtained silicone microparticles tends to decrease. On the other hand, the molecular weight is preferably not more than 200,000. Provided the molecular weight is not more than 200,000, the viscosity of the component (B) can be prevented from becoming overly high, and the production method described below can be used to easily generate silicone microparticles having a narrow particle size distribution.

In the organohydrogenpolysiloxane of the component (B1), the SiH group content is typically not more than 0.04 mol/100 g, and is preferably not more than 0.02 mol/100 g. Further, in the organohydrogenpolysiloxane of the component (B2), the SiH group content is typically not more than 0.06 mol/100 g, and is preferably not more than 0.04 mol/100 g. In those cases where the SiH group content within the component (B1) exceeds 0.04 mol/100 g, or the SiH group content within the component (B2) exceeds 0.06 mol/100 g, or both these conditions apply, the amount of the aforementioned polymethylsiloxane absorbed by the obtained silicone microparticles tends to decrease. Although there are no particular restrictions on the lower limit for the SiH group content, for practical reasons, the SiH group content in the component (B1) may be, for example, 0.001 mol/100 g or greater, and the SiH group content in the component (B2) may be, for example, 0.0015 mol/100 g or greater.

When the component (A) is component (A1), the component (B) is either component (B2) or a combination of component (B1) and component (B2). In other words, the combination where the component (A) is component (A1) and the component (B) is component (B1) is excluded from the combinations of component (A) and component (B) used for obtaining the silicone elastomer described above. This is because the elastomer cured product obtained from this combination tends to be prone to developing stickiness.

As mentioned above, the blend amount of the component (B) yields from 0.5 to 2 SiH groups within the component (B) per monovalent olefinic unsaturated group within the component (A), and this number of SiH groups is preferably within a range from 0.7 to 1.5. If an amount of the component (B) that yields fewer than 0.5 or more than 2 SiH groups is added to the liquid silicone composition, then the resulting elastomer cured product tends to develop stickiness, and also tends to exhibit reaction activity that is overly high.

Component (C)

The platinum group metal-based catalyst of the component (C) is a catalyst that promotes the addition reaction between the monovalent olefinic unsaturated groups within the component (A) and the SiH groups within the component (B). The component (C) may use either a single catalyst or a combination of two or more different catalysts.

Any of the conventional catalysts used in hydrosilylation reactions may be used as the component (C), and specific examples include platinum group metals such as platinum (including platinum black), rhodium and palladium; platinum chlorides, chloroplatinic acids and chloroplatinates such as $H_2PtCl_4 \cdot kH_2O$, $H_2PtCl_6 \cdot kH_2O$, $NaHPtCl_6 \cdot kH_2O$, $KHPtCl_6 \cdot kH_2O$, $Na_2PtCl_6 \cdot kH_2O$, $K_2PtCl_4 \cdot kH_2O$, $PtCl_4 \cdot kH_2O$, $PtCl_2$ and $Na_2HPtCl_4 \cdot kH_2O$ (wherein, k represents an integer of 0 to 6, and is preferably either 0 or 6); alcohol-modified chloroplatinic acid (see U.S. Pat. No. 3,220, 972); complexes of chloroplatinic acid and olefins (see U.S. Pat. No. 3,159,601, U.S. Pat. No. 3,159,662 and U.S. Pat. No. 3,775,452); a platinum group metal such as platinum black or palladium supported on a carrier such as alumina, silica or carbon; rhodium-olefin complexes; chlorotris(triphenylphosphine)rhodium (Wilkinson's catalyst); and complexes of a platinum chloride, a chloroplatinic acid or a chloroplatinate with a vinyl group-containing siloxane and particularly a vinyl group-containing cyclic siloxane.

The blend amount of the component (C) need only be sufficient to function as an effective hydrosilylation reaction catalyst, and the mass of the platinum group metal within the component (C) relative to the total mass of the composition, is typically within a range from 0.1 to 500 ppm, and is preferably from 0.5 to 200 ppm, and more preferably from 1 to 100 ppm.

Method of Producing Silicone Elastomer Spherical Microparticles

The silicone elastomer spherical microparticles can be produced in the form of a water dispersion using conventional methods. One possible method involves adding a surfactant and water to a mixed solution of an olefinic unsaturated group-containing organopolysiloxane and an organohydrogenpolysiloxane, performing an emulsification to generate an emulsion, and then adding a platinum group metal-based catalyst to initiate an addition reaction.

In this method, an example of the olefinic unsaturated group-containing organopolysiloxane is the component (A) described above, an example of the organohydrogenpolysiloxane is the component (B), and an example of the platinum group metal-based catalyst is the component (C).

Further, there are no particular restrictions on the surfactant, and examples include nonionic surfactants such as polyoxyethylene alkyl ethers, polyoxyethylene polyoxypropylene alkyl ethers, polyoxyethylene alkylphenyl ethers, polyethylene glycol aliphatic acid esters, sorbitan aliphatic acid esters, polyoxyethylene sorbitan aliphatic acid esters, polyoxyethylene sorbitol aliphatic acid esters, glycerol aliphatic acid esters, polyoxyethylene glycerol aliphatic acid esters, polyglycerol aliphatic acid esters, propylene glycol aliphatic acid esters, polyoxyethylene castor oils, polyoxyethylene hardened castor oils, polyoxyethylene hardened castor oil aliphatic acid esters, polyoxyethylene alkylamines, polyoxyethylene aliphatic acid amides, polyoxyethylene-modified organopolysiloxanes, and polyoxyethylene polyoxypropylene-modified organopolysiloxanes; anionic surfactants such as alkyl sulfates, polyoxyethylene alkyl ether sulfates, polyoxyethylene alkylphenyl ether sulfates, N-acyltaurinates, alkylbenzene sulfonates, polyoxyethylene alkylphenyl ether sulfonates, α-olefin sulfonates, alkylnaphthalene sulfonates, alkyl diphenyl ether disulfonates, dialkyl sulfosuccinates, monoalkyl sulfosuccinates, polyoxyethylene alkyl ether sulfosuccinates, aliphatic acid salts, polyoxyethylene alkyl ether acetates, N-acylamino acid salts, alkenylsuccinates, alkyl phosphates, polyoxyethylene alkyl ether phosphates, polystyrene sulfonates, formalin condensates of naphthalene sulfonic acid, formalin condensates of aromatic sulfonic acids, carboxylic acid polymers, and styrene oxyalkylene acid anhydride copolymers; cationic surfactants such as alkyltrimethylammonium salts, dialkyldimethylammonium salts, polyoxyethylene alkyldimethylammonium salts, dipolyoxyethylene alkylmethylammonium salts, tripolyoxyethylene alkylammonium salts, alkylbenzyldimethylammonium salts, alkylpyridinium salts, monoalkylamine salts, monoalkylamide amine salts, and cationized cellulose; and amphoteric surfactants such as alkyl dimethylamine oxides, alkyl dimethylcarboxybetaines, alkylamide propyl dimethylcarboxybetaines, alkyl hydroxysulfobetaines, and alkylcarboxymethyl hydroxyethyl imidazolinium betaines. These surfactants may be used individually, or two or more different surfactants may be used in combination. An anionic surfactant and a cationic surfactant may not be used in combination.

The emulsification can be performed using a typical emulsification disperser, examples of which include high-speed rotational centrifugal radial stirrers such as a homodisper, high-speed rotational shearing stirrers such as a homomixer, high-pressure injection-type emulsification dispersers such as a homogenizer, colloid mills, and ultrasonic emulsifiers.

In those cases where the platinum group metal-based catalyst exhibits poor dispersibility within water, the catalyst is preferably dissolved in a surfactant prior to addition to the emulsion. Examples of this surfactant include the same surfactants as those exemplified above.

The addition reaction may be conducted at room temperature, although in those cases where the reaction does not proceed to completion at room temperature, the reaction may be conducted under heating at a temperature of less than 100° C.

(Polyorganosilsesquioxane)

The silicone microparticles used in the present invention are those in which silicone elastomer spherical microparticles have been coated with a polyorganosilsesquioxane, and the amount of the polyorganosilsesquioxane is typically within a range from 0.5 to 25 parts by mass, and preferably from 1 to 15 parts by mass, per 100 parts by mass of the silicone elastomer spherical microparticles described above. If the amount of the polyorganosilsesquioxane is less than 0.5 parts by mass, then the resulting silicone microparticles may exhibit powerful cohesiveness, and the flowability, dispersibility, silkiness and smoothness of the microparticles may deteriorate. In contrast, if the amount of the polyorganosilsesquioxane exceeds 25 parts by mass, then the resulting silicone microparticles may lose their feeling of softness, and the amount of the aforementioned polymethylsiloxane absorbed may decrease.

In the silicone microparticles used in the present invention, the surface of the silicone elastomer spherical microparticles is not coated with the polyorganosilsesquioxane in such a manner that leaves absolutely no gaps in the coating. If the coating is formed with absolutely no gaps, then the silicone elastomer spherical microparticles are no longer able to absorb the polymethylsiloxane. By using the production method outlined below, surface-coated silicone microparticles can be obtained in which the surface coating includes gaps that are sufficient to allow passage of the polymethylsiloxane.

Examples of the polyorganosilsesquioxane include polymers comprising units represented by the formula $R^4SiO_{3/2}$ (wherein $R^4$ represents an unsubstituted or substituted monovalent hydrocarbon group of 1 to 20 carbon atoms, and preferably 1 to 6 carbon atoms). Specific examples of $R^4$ include alkyl groups such as a methyl group, ethyl group, propyl group, butyl group, pentyl group, hexyl group, heptyl group, octyl group, decyl group, undecyl group, dodecyl group, tetradecyl group, pentadecyl group, hexadecyl group, heptadecyl group, octadecyl group, nonadecyl group or icosyl group; alkenyl groups such as a vinyl group or allyl group; aryl groups such as a phenyl group, tolyl group or naphthyl group; aralkyl groups such as a benzyl group or phenethyl group; cycloalkyl groups such as a cyclopentyl group, cyclohexyl group or cycloheptyl group; and monovalent hydrocarbon groups in which some or all of the hydrogen atoms bonded to carbon atoms in any of the above groups have been substituted with either one or both of an atom such as a halogen atom (such as a fluorine atom, chlorine atom, bromine atom or iodine atom) and a substituent such as an amino group, acryloyloxy group, methacryloyloxy group, epoxy group, glycidoxy group, mercapto group or carboxyl group.

In order to obtain the silicone microparticles of the present invention using the production method described below, preferably not less than 50 mol % (50 to 100 mol %), more preferably not less than 70 mol % (70 to 100 mol %), and particularly preferably 80 mol % or more (80 to 100 mol %) of all the $R^4$ groups within the polyorganosilsesquioxane are methyl groups.

The polyorganosilsesquioxane may also include, besides the $R^4SiO_{3/2}$ units, at least one type of unit selected from among $R^4_2SiO_{2/2}$ units, $R^4_3SiO_{1/2}$ units and $SiO_{4/2}$ units (wherein $R^4$ is as defined above), provided the inclusion of this other type of unit does not impair the favorable feelings during use of the obtained silicone microparticles, such as feelings of silkiness or smoothness, nor impair the other properties of the silicone microparticles such as the soft feeling, the lack of cohesiveness, and the dispersibility. In this type of polyorganosilsesquioxane, the proportion of $R^4SiO_{3/2}$ units within the total number of all siloxane units is preferably within a range from 70 to 100 mol %, and is more preferably from 80 to 100 mol %.

(Production Method)

The coating of particle surfaces with another material belongs to the field of particle complexing techniques, and there are many methods therefor. When preparing the silicone microparticles used in the present invention, any conventional coating treatment method can be used, provided the effects of the resulting microparticles, namely the ability to provide favorable feelings during use and prevent shine and the like, are not impaired. Examples of these conventional methods include methods in which particles that act as the core (hereafter referred to as "core particles") and particles that are used for coating the surface of the core particles (hereafter referred to as "coating material particles") are subjected to dry mixing, thereby adhering the coating material particles to the surface of the core particles, and methods in which the mixed particles are subjected to processing that imparts an impact force, a compressive force, a frictional force or a shearing force or the like to the particles, thereby fixing the coating material particles to the surface of the core particles or forming a film of the coating particles in a physical, chemical or mechanochemical manner. However, because the silicone elastomer particles that act as the core particles exhibit powerful cohesion, adhering a uniform thin film of coating material particles to the surface of the silicone elastomer particles by dry mixing is problematic. Further, in those cases where the silicone elastomer particles exhibit a high degree of elasticity, the coating material particles may not be able to be satisfactorily fixed to the surface of the silicone elastomer particles even if an impact force, a compressive force, a frictional force or a shearing force or the like is applied to the particles. Moreover, another method exists that involves producing the coated particles by spray drying a dispersion of the core particles and the coating material particles, but this method tends to also produce aggregated particles if the concentration of the discharged liquid is too high. Accordingly, it is preferable in the present invention to use, in addition to the above method, such a method wherein the coating material particles are fixed physicochemically to the surface of the core particles within a dispersion of the core particles, as is disclosed in Patent Document 2. Moreover, in order to reduce the variations in the chemical composition and the shape within the resulting silicone microparticles, using the method disclosed in Patent Document 2 is most desirable.

A method of preparing the silicone microparticles used in the present invention is detailed below in accordance with the method disclosed in Patent Document 2. In other words, the silicone microparticles are preferably obtained by hydrolyzing and condensing an organotrialkoxysilane in a water medium, in the presence of the aforementioned silicone elastomer spherical microparticles having a volume average particle diameter within a range from 0.1 to 100 μm and an alkaline material, thereby coating the surface of the silicone elastomer spherical microparticles with a polyorganosilsesquioxane. The water medium, the silicone elastomer spherical microparticles, the alkaline material and the organotrialkoxysilane may be either added simultaneously or added at different times, although from the viewpoint of reactivity, the organotrialkoxysilane is preferably added to a water dispersion of the silicone elastomer spherical microparticles to which the alkaline material has been added. Furthermore, a method is also preferred in which the water medium and the organotrialkoxysilane are first mixed together to hydrolyze the organotrialkoxysilane, a water dispersion of the silicone elastomer spherical microparticles is then added, and the alkaline material is then added to effect the condensation reaction.

The alkaline material functions as a catalyst for the hydrolysis-condensation reaction of the organotrialkoxysilane. The alkaline material may be either a single material or a combination of two or more different materials. The alkaline material may be either added as is, or added in the form of an alkaline aqueous solution. The amount added of the alkaline material is adjusted so that the pH of the water dispersion of the silicone elastomer spherical microparticles containing the alkaline material is preferably within a range from 10.0 to 13.0, and more preferably from 10.5 to 12.5. Provided the amount of the alkaline material yields a pH within a range from 10.0 to 13.0, the hydrolysis-condensation reaction of the organotrialkoxysilane, and the coating of the surface of the silicone elastomer spherical microparticles by the polyorganosilsesquioxane both proceed favorably.

There are no particular restrictions on the alkaline material, and examples that may be used include alkali metal hydroxides such as potassium hydroxide, sodium hydroxide and lithium hydroxide; alkaline earth metal hydroxides such as calcium hydroxide and barium hydroxide; alkali metal carbonates such as potassium carbonate and sodium carbonate; ammonia; tetraalkylammonium hydroxides such as tetramethylammonium hydroxide and tetraethylammonium hydroxide; and amines such as monomethylamine, monoethylamine, monopropylamine, monobutylamine, monopentylamine, dimethylamine, diethylamine, trimethylamine, triethanolamine and ethylenediamine. Of these, ammonia is the most desirable as it can be readily removed from the powder of the resulting silicone microparticles by volatilization. Commercially available aqueous solutions of ammonia may be used as the ammonia.

Examples of the organotrialkoxysilane include compounds represented by a formula: $R^4Si(OR^5)_3$ (wherein $R^4$ is as defined above, and $R^5$ represents an unsubstituted monovalent hydrocarbon group of 1 to 6 carbon atoms). Specific examples of $R^5$ include a methyl group, ethyl group, propyl group, butyl group, pentyl group or hexyl group, although in terms of reactivity, a methyl group is preferred. In those cases where it is desirable to introduce at least one type of other unit selected from among $R^4_2SiO_{2/2}$ units, $R^4_3SiO_{1/2}$ units and $SiO_{4/2}$ units into the polyorganosilsesquioxane, at least one of the corresponding compounds, namely at least one of $R^4_2Si(OR^5)_2$, $R^4_3SiOR^5$ and $Si(OR^5)_4$, respectively, may also be added. (In the above formulas, $R^4$ and $R^5$ are as defined above). In those cases where $R^4Si(OR^5)_3$, and at least one of $R^4_2Si(OR^5)_2$, $R^4_3SiOR^5$ and $Si(OR^5)_4$ (wherein $R^4$ and $R^5$ are as defined above) are used as the raw materials for the polyorganosilsesquioxane, the proportion of the $R^4Si(OR^5)_3$ within the combined total of all the raw materials is preferably within a range from 70 to 100 mol %, and is more preferably from 80 to 100 mol %.

The amount added of the organotrialkoxysilane is adjusted so that the amount of the polyorganosilsesquioxane is typically within a range from 0.5 to 25 parts by mass, and preferably from 1 to 15 parts by mass, per 100 parts by mass of the silicone elastomer spherical microparticles.

Addition of the organotrialkoxysilane is preferably conducted under stirring using a typical stirring device such as a propeller blade or a flat blade or the like. The organotrialkoxysilane may be added in a single batch, but is preferably added gradually over a period of time in the case of a method in which the condensation reaction with the alkaline material is allowed to proceed while the organotrialkoxysilane is added. In the case where the hydrolysis reaction of the organotrialkoxysilane is performed first, and the alkaline material is then added to effect the condensation reaction, the alkaline material is preferably added and dissolved uniformly, and the stirring then halted and the reaction mixture left to stand until the condensation reaction has proceeded and the surface of the silicone elastomer spherical microparticles has been coated with the polyorganosilsesquioxane. Further, the temperature during these times is preferably within a range from 0 to 60° C., and is more preferably from 0 to 40° C. Provided this temperature is within a range from 0 to 60° C., the surface of the silicone elastomer spherical microparticles can be coated with the polyorganosilsesquioxane in a more favorable state.

After the surface of the silicone elastomer spherical microparticles has been coated with the polyorganosilsesquioxane, the reaction mixture may be heated at a temperature of approximately 40 to 100° C. to complete the hydrolysis-condensation reaction.

Following the hydrolysis-condensation reaction, water is removed from the water dispersion of the obtained silicone microparticles. This removal of the water is performed, for example, by heating the water dispersion at normal pressure or under reduced pressure following completion of the reaction, and more specific examples include a method in which the water is removed by leaving the dispersion to stand under heat, a method in which the water is removed while the dispersion is stirred and flowed under heat, a method in which the dispersion is sprayed and dispersed in a hot air stream such as by use of a spray drier, and methods that employ a fluid heating medium. Prior to this water removal operation, a pretreatment may be used to concentrate the dispersion using a method such as thermal dehydration, separation by filtration, centrifugal separation, or decantation. Moreover, if necessary, the dispersion may be washed with water.

In those cases where the product obtained upon removal of the water from the dispersion following reaction is an aggregate, the silicone microparticles can be obtained by crushing the product using a crushing device such as a jet mill, ball mill or hammer mill.

[Silicone-Based Oily Component]

The cosmetic of the present invention may include a variety of components used in typical cosmetics, provided the effects of the present invention are not impaired, and preferably includes a silicone-based oily component. This silicone-based oily component may employ a single component, or two or more components may be used in combination.

The silicone-based oily component may be any one of a solid, a semi-solid and a liquid. Examples that may be used as the silicone-based oily component include silicone oils, silicone-based surfactants, silicone resins, silicone waxes, and silicone-based gelling agents.

Examples of the silicone oils include low-viscosity to high-viscosity linear or branched organopolysiloxanes such as dimethylpolysiloxane, tristrimethylsiloxymethylsilane, caprylyl methicone, phenyl trimethicone, tetrakistrimethylsiloxysilane, methylphenylpolysiloxane, methylhexylpolysiloxane, methylhydrogenpolysiloxane and copolymers of dimethylsiloxane and methylphenylsiloxane, cyclic organopolysiloxanes such as octamethylcyclotetrasiloxane, decamethylcyclopentasiloxane, dodecamethylcyclohexasiloxane, tetramethyltetrahydrogencyclotetrasiloxane and tetramethyltetraphenylcyclotetrasiloxane, amino-modified organopolysiloxanes, pyrrolidone-modified organopolysiloxanes, pyrrolidone carboxylic acid-modified organopolysiloxanes, silicone rubbers such as gum-like dimethylpolysiloxanes having high polymerization degrees, gum-like amino-modified organopolysiloxanes and gum-like copolymers of dimethylsiloxane and methylphenylsiloxane, cyclic organopolysiloxane solutions of silicone gums or silicone rubbers, trimethylsiloxysilicates and cyclic siloxane solutions of trimethylsiloxysilicates (for example, KF-7312J and the like, manufactured by Shin-Etsu Chemical Co., Ltd.), higher alkoxy-modified silicones such as stearoxysilicone, higher fatty acid-modified silicones, alkyl-modified silicones, long chain alkyl-modified silicones, amino acid-modified silicones, fluorinated silicones, and silicone resin solutions.

Examples of the silicone-based surfactants include linear or branched polyoxyethylene-modified organopolysiloxanes, linear or branched polyoxyethylene/polyoxypropylene-modified organopolysiloxanes, linear or branched polyoxyethylene/alkyl-comodified organopolysiloxanes, linear or branched polyoxyethylene/polyoxypropylene/alkyl-comodified organopolysiloxanes, linear or branched polyglycerol-modified organopolysiloxanes, and linear or branched polyglycerol/alkyl-comodified organopolysiloxanes. (Specific examples thereof include the silicone-based emulsifiers KF-6011, 6043, 6028, 6038, 6100, 6104 and 6105 and the like, manufactured by Shin-Etsu Chemical Co., Ltd.) Furthermore, polyoxyethylene-modified partially crosslinked organopolysiloxanes and polyglycerol-modified partially crosslinked organopolysiloxanes may also be used in a mixed state with other oily components (for example, the KSG series of products: KSG-210, 710, 310, 320, 330, 340, 320Z, 350Z, 810, 820, 830, 840, 820Z and 850Z and the like, manufactured by Shin-Etsu Chemical Co., Ltd.).

Examples of the silicone resin include an acrylic silicone resin composed of an acrylic/silicone graft copolymer or an acrylic/silicone block copolymer or the like. (Specific examples thereof include the product KP-545: a cyclic organopolysiloxane solution of an acrylic/silicone graft copolymer, manufactured by Shin-Etsu Chemical Co., Ltd.) Furthermore, acrylic silicone resins containing at least one portion selected from the group consisting of pyrrolidone portions, long-chain alkyl portions, polyoxyalkylene portions and anion portions such as fluoroalkyl portions and carboxylic acid portions within each molecule may also be used. Moreover, the silicone resin is preferably a silicone network-type compound formed from at least one resin selected from amongst resins composed of $R^8{}_3SiO_{0.5}$ units and $SiO_2$ units, resins composed of $R^8{}_3SiO_{0.5}$ units, $R^8{}_2SiO$ units and $SiO_2$ units, resins composed of $R^8{}_3SiO_{0.5}$ units and $R^8SiO_{1.5}$ units, resins composed of $R^8{}_3SiO_{0.5}$ units, $R^8{}_2SiO$ units and $R^8SiO_{1.5}$ units, and resins composed of $R^8{}_3SiO_{0.5}$ units, $R^8{}_2SiO$ units, $R^8SiO_{1.5}$ units and $SiO_2$ units. In these formulas, $R^8$ represents a substituted or unsubstituted monovalent hydrocarbon group of 1 to 30 carbon atoms. Furthermore, a silicone network-type compound containing at least one portion selected from the group consisting of pyrrolidone portions, long-chain alkyl portions, polyoxyalkylene portions, polyglycerol portions, fluoroalkyl portions and amino portions within each molecule may also be used. In those cases where a silicone resin such as an acrylic silicone resin or silicone network-type compound is used, the blend amount is preferably within a range from 0.1 to 20% by mass, and more preferably from 1 to 10% by mass, of the entire mass of the cosmetic.

Examples of the silicone wax include an acrylic silicone wax formed from an acrylic/silicone graft copolymer or an acrylic/silicone block copolymer or the like. (Specific examples thereof include the products KP-561P, 562P and the like: cyclic organopolysiloxane solutions of an acrylic/silicone graft copolymer, manufactured by Shin-Etsu Chemical Co., Ltd.) Further more, acrylic silicone waxes containing at least one portion selected from the group consisting of pyrrolidone portions, long-chain alkyl portions, polyoxyalkylene portions, and anion portions such as fluoroalkyl portions and carboxylic acids within each molecule may also be used. Furthermore, this silicone wax is preferably a polylactone-modified polysiloxane having a bonded polylactone, which is a ring-opening polymerization product of a lactone compound having a 5-membered ring or higher. Moreover, the silicone wax may also be a silicone-modified olefin wax obtained by performing an addition reaction between an olefin wax having unsaturated groups formed from an α-olefin and a diene, and an organohydrogenpolysiloxane having one or more SiH bonds within each molecule. The α-olefin is preferably an α-olefin of 2 to 12 carbon atoms such as ethylene, propylene, 1-butene, 1-hexene or 4-methyl 1-pentene, and the diene is preferably butadiene, isoprene, 1,4-hexadiene, vinylnorbornene, ethylidene norbornene or dicyclopentadiene or the like. The organohydrogenpolysiloxane having one or more SiH bonds may have a linear structure or a siloxane branched structure.

Examples of the silicone-based gelling agents include gel mixtures containing a gelling component such as an unmodified or modified partially crosslinked organopolysiloxane such as an unmodified partially crosslinked organopolysiloxane, an alkyl-modified partially crosslinked organopolysiloxane or a silicone branched alkyl-modified partially crosslinked organopolysiloxane, and a variety of oil components such as cyclopentasiloxane, dimethicone, mineral oil, isododecane, trioctanoin or squalane. The above gelling component and the oil component coexist within the gel mixture. Specific examples of this type of gel mixture include the KSG series (product name), and particularly KSG-15, 16, 41, 42, 43, 44, 042Z and 045Z (all product names) manufactured by Shin-Etsu Chemical Co., Ltd.

In the cosmetic of the present invention, the blend amount of the silicone-based oily component is preferably within a range from 1 to 98% by mass of the entire cosmetic.

[Oily Gel Composition]

As described above, the silicone microparticles used in the present invention may be included in the cosmetic of the present invention, as is, as a cosmetic component, although in order to let the cosmetic exert the desired feelings during use, it is preferable to prepare an oily gel composition containing the silicone microparticles and an aforementioned silicone-based oily component separately and to prepare the cosmetic including the silicone microparticles and the silicone-based oily component as the oily gel composition. A cosmetic generally includes a combination of a variety of silicone-based oily components. In the process for producing a cosmetic, if the silicone microparticles alone are added to a mixture of the silicone-based oily components, then the swelling properties of the silicone microparticles manifest relative to the mixture. In contrast, even if the final silicone-based oily component formulation is the same, a cosmetic having the required feelings during use can be obtained by beforehand controlling the swelling of the silicone microparticles using a portion of the silicone-based oily components. In other words, by beforehand forming an oily gel composition comprising the silicone microparticles and a portion of the silicone-based oily components to be included within the cosmetic, where the portion of the silicone-based oily components suppress the swelling of the silicone microparticles, swelling of the silicone microparticles can be suppressed, and by using such an oily gel composition, a cosmetic that exhibits a powdery sensation when used can be obtained. In contrast, by beforehand forming an oily gel composition comprising the silicone microparticles and those silicone-based oily components that exhibit significant swelling properties, the swelling of the silicone microparticles can be enhanced, and by using such an oily gel composition, a cosmetic that exhibits a silky feel, and a cosmetic that yields a soft and elastic film can be obtained.

In the oily gel composition, the silicone-based oily component is in a structured state produced by the silicone microparticles used in the present invention. The description of the silicone-based oily component as being in a "structured state" means that the silicone-based oily component is in a hardened state, a gelled state, a paste-like state, or simply a state of increased viscosity. In other words, due to its own weight, the silicone-based oily component that exists in a structured state produced by the silicone microparticles used in the present invention does not drain from the silicone microparticles. An silicone-based oily component that has been converted to a gel-like state or a paste-like state by the silicone microparticles used in the present invention exhibits increased viscosity. Further, the above description of a hardened state, a gelled state, a paste-like state, or simply a state of increased viscosity, refers to the state for a temperature at which the silicone-based oily component is a liquid, although at normal temperatures the silicone-based oily component may be any one of a liquid, a semi-solid or a solid. In other words, even if the silicone-based oily component is a semi-solid or solid at room temperature, provided it is a silicone-based oily component that can be converted to a liquid form by heating to a certain temperature (such as a silicone-modified wax), it can be converted to a hardened state, a gelled state, a paste-like state, or simply a state of increased viscosity by the silicone microparticles used in the present invention.

There are no particular restrictions on the method used for preparing the oily gel composition. If the silicone-based oily component is a liquid at room temperature, then the oily gel composition can be obtained simply by stirring and mixing the silicone microparticles used in the present invention and the silicone-based oily component. By performing stirring and mixing, the silicone microparticles are dispersed within the silicone-based oily component as the silicone microparticles absorb the silicone-based oily component, forming a state of poor fluidity, namely a state in which the silicone-based oily component is in a "structured state." Further, in those cases where a silicone-based oily component that is either a semi-solid or a solid at room temperature is used, the oily gel composition can be obtained by stirring and mixing the silicone microparticles used in the present invention and the silicone-based oily component at a temperature where the silicone-based oily component can be converted to a liquid state. The stirring need not necessarily impart a shearing force, and need only provide sufficient force to disperse the silicone microparticles uniformly within the silicone-based oily component. Examples of stirring devices that may be used include a propeller blade, flat blade, anchor mixer, planetary mixer, or kneader-extruder or the like.

The ratio between the silicone microparticles and the silicone-based oily component within the oily gel composition, reported as a mass ratio, is preferably within a range from 5/95 to 90/10.

A single oily gel composition may be used alone, or two or more compositions may be used in combination. In the cosmetic of the present invention, the blend amount of the oily gel composition is preferably within a range from 1.1 to 98.1% by mass of the entire cosmetic.

[Cosmetically Acceptable Carriers]

The cosmetic of the present invention preferably further comprises a cosmetically acceptable carrier, wherein the oily gel composition is mixed with the carrier. Either a single carrier may be used alone, or two or more carriers may be used in combination. In this description, the "carrier" means aforementioned cosmetically acceptable silicone-based oily components that are able to be mixed with the oily gel composition, and components that are other than the aforementioned cosmetically acceptable silicone-based oily components and that are able to be mixed with the oily gel composition. Examples of these components that are other than the aforementioned cosmetically acceptable silicone-based oily components and that are able to be mixed with the oily gel composition include (a) unctuous agents, (b) water, (c) compounds having an alcoholic hydroxyl group, (d) water-soluble or water-swellable polymer compounds, (e) particles other than the silicone microparticles, (f) surfactants, and other additives.

((a) Unctuous Agents)

The unctuous agent of component (a) may be any of a solid, a semi-solid and a liquid. Examples that may be used as unctuous agents include natural animal or plant oils and fats, semi-synthetic oils and fats, hydrocarbon oils, higher alcohols, ethers, ester oils, glyceride oils, and fluorine-containing unctuous agents.

Examples of the natural animal or plant oils and fats and semi-synthetic oils and fats include avocado oil, linseed oil, almond oil, ibota wax, perilla oil, olive oil, cacao butter, kapok wax, kaya oil, carnauba wax, liver oil, candelilla wax, refined candelilla wax, beef tallow, neat's-foot tallow, beef bone tallow, hardened beef tallow, apricot kernel oil, whale wax, hardened oil, wheat germ oil, sesame oil, rice genii oil, rice bran oil, sugarcane wax, camellia sasanqua oil, safflower oil, shea butter, Chinese tungoil, cinnamon oil, jojoba wax, squalane, squalene, shellac wax, turtle oil, soybean oil, tea berry oil, camellia oil, evening primrose oil, corn oil, lard, rapeseed oil, Japanese tung oil, bran wax, germ oil, horse tallow, persic oil, palm oil, palm kernel oil, castor oil, hardened castor oil, castor oil fatty acid methyl ester, sunflower oil, grapeseed oil, bayberry wax, jojoba oil, macadamia nut oil, beeswax, mink oil, meadowfoam oil, cottonseed oil, cotton wax, Japan wax, Japan wax kernel oil, montan wax, coconut oil, hardened coconut oil, tri(coconut oil fatty acid) glyceride, mutton tallow, peanut oil, lanolin, liquid lanolin, reduced lanolin, lanolin alcohol, hard lanolin, lanolin acetate, lanolin alcohol acetate, lanolin fatty acid isopropyl ester, polyoxyethylene lanolin alcohol ether, polyoxyethylene lanolin alcohol acetate, lanolin fatty acid polyethylene glycol, polyoxyethylene hydrogenated lanolin alcohol ether, and egg-yolk oil.

Examples of the hydrocarbon oils include linear and branched hydrocarbon oils, and include both volatile hydrocarbon oils and non-volatile hydrocarbon oils. Specific examples of these hydrocarbon oils include synthetic squalane, plant-based squalane, squalene, liquid isoparaffin, light isoparaffin, hydrogenated polyisobutene, isododecane, light liquid isoparaffin, isohexadecane, liquid paraffin, pristane, α-olefin oligomers, ozokerite, ceresin, paraffin, paraffin wax, polyethylene wax, polyethylene-polypropylene wax, (ethylene-propylene-styrene) copolymers, (butylene-propylene-styrene) copolymers, polyisobutylene, microcrystalline wax and Vaseline.

Examples of the higher alcohols include alcohols in which the number of carbon atoms is preferably at least 6, and more preferably within a range from 10 to 30. Specific examples of these higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecynol, cholesterol, phytosterol, polyoxyethylene cholesterol ether, monostearyl glycerol ether (batyl alcohol), and monooleyl glyceryl ether (selachyl alcohol).

Examples of the ethers include monoalkyl and dialkyl ethers of ethylene glycol, diethylene glycol and triethylene glycol, monoalkyl and dialkyl ethers of butylene glycol, propylene glycol, dipropylene glycol, pentylene glycol and caprylyl glycol, monoalkyl, dialkyl and trialkyl ethers of glycerol, and alkyl ethers of isononyl alcohol, caprylyl alcohol and stearyl alcohol.

Examples of the ester oils include dioctyl succinate, diisobutyl adipate, dioctyl adipate, di(2-heptylundecyl) adipate, diisopropyl sebacate, dioctyl sebacate, dibutyloctyl sebacate, diisostearyl malate, triethyl citrate, ethylene glycol dioctanoate, neopentyl glycol dioctanoate, propylene glycol dicaprate, neopentyl glycol dicaprate, trimethylolpropane trioctanoate, trimethylolpropane triisostearate, pentaerythritol tetraoleate, ethyl acetate, butyl acetate, amyl acetate, octyldodecyl neopentanoate, cetyl octanoate, isononyl isononanoate, isotridecyl isononanoate, hexyldecyl dimethyloctanoate, ethyl laurate, hexyl laurate, isopropyl myristate, myristyl myristate, isocetyl myristate, octyldodecyl myristate, isopropyl palmitate, octyl palmitate, cetyl palmitate, isocetyl palmitate, isostearyl palmitate, butyl stearate, hexyldecyl stearate, isopropyl isostearate, isocetyl isostearate, decyl oleate, oleyl oleate, octyldodecyl oleate, ethyl linoleate, isopropyl linoleate, cetyl lactate, myristyl lactate, cholesteryl hydroxystearate, dioctyldodecyl lauroyl glutamate, isopropyl lauroyl sarcosinate, and octyldodecyl gum ester.

Examples of the glyceride oils include acetoglyceryl, glyceryl triisooctanoate, glyceryl trimyristate, glyceryl triisopalmitate, glyceryl triisostearate, glyceryl tribehenate, glyceryl diisostearate, glyceryl monostearate, diglyceryl (isostearate-myristate), and pentaerythritol fatty acid esters.

Examples of the fluorine-containing unctuous agents include perfluoropolyether, perfluorodecalin and perfluorooctane.

The blend amount of the unctuous agent of component (a) varies depending on the form of the cosmetic of the present invention, but is preferably selected appropriately from within a range from 1 to 98% by mass of the entire cosmetic.

((b) Water)

The blend amount of the water of component (b) varies depending on the form of the cosmetic of the present invention, but is preferably selected appropriately from within a range from 1 to 95% by mass of the total mass of the cosmetic.

((c) Compounds Having an Alcoholic Hydroxyl Group)

Examples of the compound having an alcoholic hydroxyl group of component (c) include lower alcohols (lower monohydric alcohols) preferably containing from 2 to 5 carbon atoms, such as ethanol and isopropanol, and sugar alcohols such as sorbitol and maltose. Additional examples include sterols such as cholesterol, sitosterol, phytosterol and lanosterol, and polyhydric alcohols such as butylene glycol, propylene glycol, dibutylene glycol and pentylene glycol. The blend amount of the component (c) is preferably selected appropriately from within a range from 0.1 to 98% by mass of the cosmetic of the present invention.

((d) Water-Soluble or Water-Swellable Polymer Compounds)

Examples of the water-soluble or water-swellable polymer compound of component (d) include plant-based polymer compounds such as gum arabic, tragacanth gum, galactan, carob gum, guar gum, karaya gum, carageenan, pectin, agar, quince seed (marmelo), starch (from rice, corn, potato or wheat and the like), algae colloids, trant gum and locust bean gum, microbe-derived polymer compounds such as xanthan gum, dextran, succinoglycan and pullulan, animal-based polymer compounds such as collagen, casein, albumin and gelatin, starch-based polymer compounds such as carboxymethyl starch and methylhydroxypropyl starch, cellulose-based polymer compounds such as methyl cellulose, ethyl cellulose, methyl hydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose and cellulose powders, alginic acid-based polymer compounds such as sodium alginate and propylene glycol alginic acid ester, vinyl-based polymer compounds such as polyvinyl methyl ether and carboxyvinyl polymers, polyoxyethylene-based polymer compounds, polyoxyethylene-polyoxypropylene copolymer compounds, acrylic polymer compounds such as sodium polyacrylate, polyethyl acrylate, polyacrylamide and acryloyldimethyl taurate copolymers, synthetic water-soluble polymer compounds such as polyethyleneimine and cation polymers, and inorganic water-soluble polymer compounds such as bentonite, aluminum magnesium silicate, montmorillonite, beidellite, nontronite, saponite, hectorite and anhydrous silicic acid. Examples of the component (d) also include film-forming agents such as polyvinyl alcohol and polyvinylpyrrolidone. The blend amount of the component (d) is preferably within a range from 0.1 to 25% by mass of the cosmetic of the present invention.

((e) Particles Other than the Silicone Microparticles)

Examples of the particles of component (e) include particles other than the silicone microparticles, including inorganic particles, organic particles, inorganic-organic composite powders, and silicone resin particles.

Examples of the inorganic particles include microparticles composed of titanium oxide, titanated mica, zirconium oxide, zinc oxide, cerium oxide, magnesium oxide, barium sulfate, calcium sulfate, magnesium sulfate, calcium carbonate, magnesium carbonate, talc, cleaved talc, mica, kaolin, sericite, muscovite, synthetic mica, phlogopite, lepidolite, biotite, lithia mica, silicic acid, silicon dioxide, fumed silica, hydrous silicon dioxide, aluminum silicate, magnesium silicate, aluminum magnesium silicate, calcium silicate, barium silicate, strontium silicate, metal tungstenate salts, hydroxyapatite, vermiculite, higilite, bentonite, montmorillonite, hectorite, zeolite, ceramics, dicalcium phosphate, alumina, aluminum hydroxide, boron nitride, boron nitride or glass.

Examples of the inorganic particles further include pigment-based inorganic microparticles. Specific examples include inorganic red pigments such as iron oxide, iron hydroxide and iron titanate, inorganic brown pigments such as γ-iron oxide, inorganic yellow pigments such as iron oxide yellow and yellow ocher, inorganic black pigments such as iron oxide black and carbon black, inorganic violet pigments such as manganese violet and cobalt violet, inorganic green pigments such as chromium hydroxide, chromium oxide, cobalt oxide, and cobalt titanate, inorganic blue pigments such as Prussian blue and ultramarine blue, colored pigments such as lakes of tar-based colorants and lakes of natural dyes, and pearl pigments such as titanium oxide-coated mica, bismuth oxychloride, titanium oxide-coated bismuth oxychloride, titanium oxide-coated talc, dew pearl and titanium oxide-coated colored mica.

Moreover, examples of the inorganic particles also include metal microparticles consisting of aluminum, copper, stainless steel, silver or the like.

Examples of the organic particles include powders composed of a polyamide, polyacrylic acid/acrylic acid ester, polyester, polyethylene, polypropylene, polystyrene, styrene/acrylic acid copolymer, divinylbenzene/styrene copolymer, polyurethane, vinyl resin, urea resin, melamine resin, benzoguanamine, polymethylbenzoguanamine, tetrafluoroethylene, polymethylmethacrylate (such as poly(methyl methacrylate)), cellulose, silk, nylon, phenol resin, epoxy resin or polycarbonate.

Furthermore, other examples of the organic particles include metal salt surfactant powders (metal soaps), specific examples of which include zinc stearate, aluminum stearate, calcium stearate, magnesium stearate, zinc myristate, magnesium myristate, zinc cetylphosphate, calcium cetylphosphate and zinc sodium cetylphosphate.

Examples of the organic particles further include organic colorants, and specific examples include tar colorants such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206 and Orange No. 207, and natural colorants such as carminic acid, laccaic acid, carthamin, brazilin and crocin.

Examples of the inorganic-organic composite powders include complex powders obtained by using a conventional method to coat the surface of an inorganic powder typically used within cosmetic products with an organic powder.

Examples of the silicone resin particles include silicone elastomer particles, polymethylsilsesquioxane particles, and particles prepared by coating the surface of silicone elastomer particles with a polymethylsilsesquioxane.

Particles that can also be used other than the silicone microparticles described above include those that have been subjected to a surface treatment using a silane or silylation agent such as a caprylsilane (AES-3083, manufactured by Shin-Etsu Chemical Co., Ltd.), a silicone oil such as a dimethylsilicone (KF-96 AK series, manufactured by Shin-Etsu Chemical Co., Ltd), methylhydrogenpolysiloxane (such as KF-99P and KF-9901, manufactured by Shin-Etsu Chemical Co., Ltd.) or silicone-branched silicone treatment agent (such as KF-9908 and KF-9909, manufactured by Shin-Etsu Chemical Co., Ltd.), a wax, a paraffin, an organofluorine compound such as a perfluoroalkyl phosphate, a surfactant, an amino acid such as N-acylglutamic acid, or a metal soap such as aluminum stearate or magnesium myristate.

((f) Surfactants)

Surfactants can be classified into nonionic, anionic, cationic and amphoteric surfactants, and examples of the surfactant of component (f) include those that can be used in the production of a water dispersion of the above silicone elastomer spherical microparticles.

(Other Additives)

Examples of other additives include oil-soluble gelling agents, antiperspirants, ultraviolet absorbers, ultraviolet absorption and scattering agents, moisturizers, antibacterial preservatives, fragrances, salts, antioxidants, pH modifiers, chelating agents, algefacients, anti-inflammatory agents, skin beautifying components (such as whitening agents, cell activators, rough skin improvers, blood circulation promoters, skin astringents and anti-seborrheic agents), vitamins, amino acids, nucleic acids, hormones, clathrate compounds and hair-setting agents.

Examples of the oil-soluble gelling agents include metal soaps such as aluminum stearate, magnesium stearate and zinc myristate, amino acid derivatives such as N-lauroyl-L-glutamic acid and α,γ-di-n-butylamine, dextrin fatty acid esters such as dextrin palmitic acid ester, dextrin stearic acid ester and dextrin 2-ethylhexanoic acid palmitic acid ester, sucrose fatty acid esters such as sucrose palmitic acid ester and sucrose stearic acid ester, fructooligosaccharide fatty acid esters such as fructooligosaccharide stearic acid ester and fructooligosaccharide 2-ethylhexanoic acid ester, benzylidene derivatives of sorbitol such as monobenzylidene sorbitol and dibenzylidene sorbitol, and organic-modified clay minerals such as dimethylbenzyldodecylammonium montmorillonite clay and dimethyldioctadecylammonium montmorillonite clay.

Examples of the antiperspirants include aluminum chlorohydrate, aluminum chloride, aluminum sesquichlorohydrate, zirconyl hydroxychloride, aluminum zirconium hydroxychloride, and aluminum zirconium glycine complex.

Examples of the ultraviolet absorbers include benzoic acid-based ultraviolet absorbers such as para-aminobenzoic acid, anthranilic acid-based ultraviolet absorbers such as methyl anthranilate, salicylic acid-based ultraviolet absorbers such as methyl salicylate, octyl salicylate and trimethylcyclohexyl salicylate, cinnamic acid-based ultraviolet absorbers such as octyl para-methoxycinnamate, benzophenone-based ultraviolet absorbers such as 2,4-dihydroxybenzophenone, urocanic acid-based ultraviolet absorbers such as ethyl urocanate, dibenzoylmethane-based ultraviolet absorbers such as 4-t-butyl-4'-methoxy-dibenzoylmethane, as well as phenylbenzimidazole sulfonic acid and triazine derivatives.

Examples of the ultraviolet absorption and scattering agents include particles that are capable of absorbing and scattering ultraviolet light, such as microparticulate titanium oxide, microparticulate iron-containing titanium oxide, microparticulate zinc oxide, microparticulate cerium oxide, and complexes thereof. A dispersion prepared in advance by dispersing these types of particles capable of absorbing and scattering ultraviolet light in an unctuous agent may also be used.

Examples of moisturizers include glycerol, sorbitol, propylene glycol, dipropylene glycol, 1,3-butylene glycol, pentylene glycol, glucose, xylitol, maltitol, polyethylene glycol, hyaluronan, chondroitin sulfate, pyrrolidone carboxylate, polyoxyethylene methyl glucoside, polyoxypropylene methyl glucoside, egg yolk lecithin, soybean lecithin, phosphatidylcholine, phosphatidylethanolamine, phosphatidylserine, phosphatidylglycerol, phosphatidylinositol, and sphingophospholipid.

Examples of the antibacterial preservatives include alkyl paraoxybenzoic acid esters, benzoic acid, sodium benzoate, sorbic acid, potassium sorbate and phenoxyethanol. Examples of antibacterial agents include benzoic acid, salicylic acid, carbolic acid, sorbic acid, alkyl paraoxybenzoic acid esters, parachlorometacresol, hexachlorophene, benzalkonium chloride, chlorhexidine chloride, trichlorocarbanilide, photosensitizers and phenoxyethanol.

Examples of the fragrances include natural fragrances and synthetic fragrances. Examples of the natural fragrances include plant-based fragrances isolated from flowers, leaves, wood materials and fruit skins, and animal-based fragrances such as musk and civet. Examples of the synthetic fragrances include hydrocarbons such as monoterpenes, alcohols such as aliphatic alcohols and aromatic alcohols, aldehydes such as terpene aldehydes and aromatic aldehydes, ketones such as alicyclic ketones, esters such as terpene-based esters, lactones, phenols, oxides, nitrogen-containing compounds, and acetals.

Examples of the salts include inorganic salts, organic acid salts, amine salts and salts of amino acids. Examples of the inorganic salts include the sodium salts, potassium salts, magnesium salts, calcium salts, aluminum salts, zirconium salts and zinc salts of inorganic acid such as hydrochloric acid, sulfuric acid, carbonic acid and nitric acid. Examples of the organic acid salts include salts of organic acids such as acetic acid, dehydroacetic acid, citric acid, malic acid, succinic acid, ascorbic acid and stearic acid. Examples of the amine salts include salts of amines such as triethanolamine. Examples of the amino acid salts include salts of amino acids such as glutamic acid. Other salts that may be used include salts of hyaluronic acid and chondroitin sulfuric acid, aluminum zirconium glycine complexes, and salts produced by acid-alkaline neutralization within the cosmetic formulation.

Examples of the antioxidants include tocopherol, p-t-butylphenol, butylhydroxyanisole, dibutylhydroxytoluene and phytic acid.

Examples of the pH modifiers include lactic acid, citric acid, glycolic acid, succinic acid, tartaric acid, dl-malic acid, potassium carbonate, sodium hydrogen carbonate and ammonium hydrogen carbonate.

Examples of the chelating agents include alanine, sodium ethylenediamine tetraacetate, sodium polyphosphate, sodium metaphosphate and phosphoric acid.

Examples of the algefacients include L-menthol and camphor.

Examples of the anti-inflammatory agents include allantoin, glycyrrhizinic acid and salts thereof, glycyrrhetinic acid and stearyl glycyrrhetinate, tranexamic acid and azulene.

Examples of the skin beautifying components include whitening agents such as placenta extract, arbutin, glutathione and Yukinoshita extract, cell activators such as royal jelly, photosensitizers, cholesterol derivatives and calf blood extract, rough skin improvers, blood circulation promoters such as nonylic acid vanillylamide, benzyl nicotinic acid ester, β-butoxyethyl nicotinic acid ester, capsaicin, zingerone, cantharis tincture; ichthammol, caffeine, tannic acid, α-borneol, tocopherol nicotinate, inositol hexanicotinate, cyclandelate, cinnarizine, tolazoline, acetylcholine, verapamil, cepharanthine and γ-orizanol, skin astringents such as zinc oxide and tannic acid, and anti-seborrheic agents such as sulfur and thianthol.

Examples of the vitamins include A vitamins such as vitamin A oil, retinol, retinol acetate and retinol palmitate, B vitamins, including vitamin $B_2$ such as riboflavin, riboflavin butyrate and flavin adenine nucleotide, vitamin $B_6$ such as pyridoxine hydrochloride, pyridoxine dioctanoate and pyridoxine tripalmitate, vitamin $B_{12}$ and derivatives thereof, and vitamin $B_{15}$ and derivatives thereof, C vitamins such as L-ascorbic acid, L-ascorbic acid dipalmitic acid ester, sodium L-ascorbate-2-sulfate and dipotassium L-ascorbic acid diphosphoric acid ester, D vitamins such as ergocalciferol and cholecalciferol, E vitamins such as α-tocopherol, β-tocopherol, γ-tocopherol, dl-α-tocopherol acetate, dl-α-tocopherol nicotinate and dl-α-tocopherol succinate, nicotinic acids such as nicotinic acid, benzyl nicotinate and nicotinic acid amide, vitamin H, vitamin P, pantothenic acids such as calcium pantothenate, D-pantothenyl alcohol, pantothenyl ethyl ether and acetylpantothenyl ethyl ether, and biotin.

Examples of the amino acids include glycine, valine, leucine, isoleucine, serine, threonine, phenylalanine, alginine, lysine, aspartic acid, glutamic acid, cystine, cysteine, methionine and tryptophan.

Examples of the nucleic acids include deoxyribonucleic acid.

Examples of the hull ones include estradiol and ethenylestradiol.

Examples of the clathrate compounds include cyclodextrin.

Examples of the hair-setting agents include amphoteric, anionic, cationic and nonionic polymer compounds, including polyvinylpyrrolidone-based polymers such as polyvinylpyrrolidone and vinylpyrrolidone/vinyl acetate copolymers, acidic vinyl ether-based polymer compounds such as methyl vinyl ether/maleic anhydride alkyl half-ester copolymers, acidic polyvinyl acetate-based polymer compounds such as vinyl acetate/crotonic acid copolymers, acidic acrylic polymer compounds such as (meth)acrylic acid/alkyl (meth) acrylate copolymers and (meth)acrylic acid/alkyl (meth) acrylate/alkyl acrylamide copolymers, and amphoteric acrylic polymer compounds such as N-methacryloylethyl-N, N-dimethylammonium α-N-methylcarboxybetaine/alkyl (meth)acrylate copolymers and hydroxypropyl (meth)acrylate/butylaminoethyl methacrylate/octylamide acrylate copolymers. Furthermore, naturally occurring polymer compounds such as cellulose or derivatives thereof, keratin or derivatives thereof, and collagen or derivatives thereof can also be used favorably.

EXAMPLES

A more detailed description of the present invention is presented below based on a series of examples and comparative examples, although the present invention is in no way limited by these examples. In the examples, unless stated otherwise, "%" values representing concentration or content refer to "% by mass". Furthermore, a "dimethylsiloxane unit content" refers to the proportion (mol %) of dimethylsiloxane units represented by the formula: —$(CH_3)_2SiO$— relative to all the non-terminal siloxane units within the polysiloxane that corresponds with the component (A) or the component (B).

Production Example 1

Production of Silicone Microparticles-1

A glass beaker with a capacity of 1 liter was charged with 350 g of a methylvinylpolysiloxane A1 represented by formula (3) shown below and having a dimethylsiloxane unit content of 100 mol %, a molecular weight of 13,524 and a vinyl group content of 0.015 mol/100 g, and 160 g of a methylhydrogenpolysiloxane B1 represented by formula (4) shown below and having a dimethylsiloxane unit content of 98.7 mol %, a molecular weight of 11,369 and a SiH group content of 0.035 mol/100 g (an amount equivalent to 1.07 SiH groups within the methylhydrogenpolysiloxane B1 per vinyl group within the methylvinylpolysiloxane A1), and stirring and mixing were performed at 2,000 rpm using a homomixer. To the resulting mixed liquid were added 1.2 g of a polyoxyethylene lauryl ether (number of mols of added ethylene oxide=9 mol) and 100 g of water, and subsequent stirring at 6,000 rpm using the homomixer yielded an O/W type emulsion of increased viscosity. Stirring was continued for a further 15 minutes. Subsequently, with the stirring continued at 2,000 rpm, 385 g of water was added, yielding a uniform white emulsion. This emulsion was transferred to a glass flask with a capacity of 1 liter fitted with a stirring device having an anchor-shaped stirring blade, and following adjustment of the temperature to a value of 15 to 20° C., a mixed solution containing 0.8 g of a toluene solution of a chloroplatinic acid-olefin complex (platinum content: 0.5%), 1.5 g of a polyoxyethylene lauryl ether (number of mols of added ethylene oxide=4 mol), and 1.5 g of a polyoxyethylene lauryl ether (number of mols of added ethylene oxide=23 mol) was added to the flask under constant stirring. Stirring was then continued at the same temperature for 12 hours, thus forming a water dispersion of silicone elastomer microparticles. Inspection of the shape of these silicone elastomer microparticles under an optical microscope revealed that the particles were spherical, and measurement of the volume average particle diameter using a particle size distribution measuring apparatus "Multisizer 3" (a product name, manufactured by Beckman Coulter, Inc.) yielded a result of 12 μm.

882 g of the thus obtained water dispersion of silicone elastomer spherical microparticles was transferred to a glass flask with a capacity of 3 liters fitted with a stirring device having an anchor-shaped stirring blade, and 2,003 g of water and 57 g of 28% ammonia water were added to the flask. The pH of the liquid at this point was 11.2. Following lowering of the temperature to 5 to 10° C., 58 g of methyltrimethoxysilane (an amount that yields 6.3 parts by mass of a polymethylsilsesquioxane following the hydrolysis and condensation reaction per 100 parts by mass of the silicone elastomer spherical microparticles) was added dropwise to the flask over a period of 25 minutes, and stirring was then continued for a further 1 hour. During this period, the liquid temperature was maintained at 5 to 10° C. Subsequently, the reaction mixture was heated to 55 to 60° C., and stirring was continued at this temperature for 1 hour to complete the hydrolysis-condensation reaction of the methyltrimethoxysilane.

The obtained methyltrimethoxysilane hydrolysis-condensation reaction liquid was filtration-dewatered using a pressure filtration device. The dewatered product was transferred to a stainless steel tray and dried at a temperature of 105° C. in a hot air circulating drier. The resulting dried product was crushed in a jet mill, yielding microparticles with good flowability. Inspection of these microparticles using an electron microscope revealed spherical particles, the surfaces of which were coated with particulate matter with a particle diameter of approximately 100 nm, confirming that silicone microparticles comprising the silicone elastomer spherical microparticles coated with a polyorganosilsesquioxane had been obtained. The thus obtained silicone microparticles were dispersed in water using a surfactant, and subsequent measurement of the volume average particle diameter using a Multisizer 3 yielded a result of 12 μm. The obtained silicone microparticles are referred to as Silicone microparticles-1.

The methylvinylpolysiloxane A1, the methylhydrogenpolysiloxane B1, and the toluene solution of a chloroplatinic acid-olefin complex (platinum content: 0.5%) were mixed together in the same proportions as those used above in preparing the silicone elastomer spherical microparticles, and the resulting mixture was poured into an aluminum Petri dish in an amount sufficient to generate a thickness of 10 mm. The mixture was left to stand at 25° C. for 24 hours, and was then heated for 1 hour in a thermostatic chamber at 50° C., thus forming a non-sticky silicone elastomer. Measurement of the hardness of this silicone elastomer using a type A durometer prescribed in JIS K 6253 revealed a result of 22.

The methylvinylpolysiloxane A1, the methylhydrogenpolysiloxane B1, and the toluene solution of a chloroplatinic acid-olefin complex (platinum content: 0.5%) were mixed together in the same proportions as those used above in preparing the silicone elastomer spherical microparticles, and the resulting mixture was poured onto a Teflon (a registered trademark) tray in an amount sufficient to generate a thickness of approximately 1 mm. The mixture was left to stand at 25° C. for 24 hours, and was then heated for 1 hour in a thermostatic chamber at 50° C., thus forming a silicone elastomer sheet. Test pieces were prepared by cutting the obtained sheet into square pieces with a length along one side of approximately 30 mm, and following measurement of the mass of these test pieces, each test piece was immersed for 24 hours in one of the polymethylsiloxanes shown in Table 1. This caused the test piece to absorb the polymethylsiloxane and swell. Each test piece was then removed from the polymethylsiloxane, and following removal of any polymethylsiloxane on the test piece surface by wiping with a tissue, the mass of the test piece was re-measured. Table 1 lists the amount of the polymethylsiloxane absorbed (the oil absorption amount) by the silicone elastomer sheet per 1 g of the silicone elastomer.

5.0 g of Silicone microparticles-1 and 50 g of a polymethylsiloxane shown in Table 1 were placed in a 100 ml glass bottle, and after shaking for 30 minutes, the bottle was left to stand for 3 days at room temperature. A solid-liquid separation was then performed using pressure filtration, and the mass of the resulting cake-like solid fraction was measured. Table 1 lists the oil absorption amount per 5 g of the silicone microparticles, which was calculated using the formula: [mass (g) of solid fraction following solid-liquid separation]– 5.0 (g).

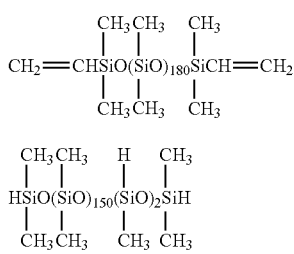

$$CH_2\!\!=\!\!CHSiO(SiO)_{180}SiCH\!\!=\!\!CH_2 \quad (3)$$
with CH₃ groups

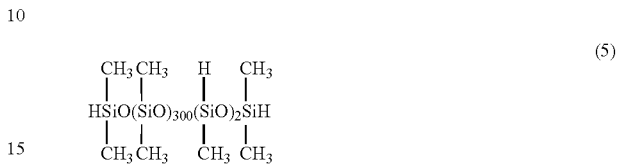

(4) HSiO(SiO)₁₅₀(SiO)₂SiH with CH₃, H, CH₃ substituents

Production Example 2

Production of Silicone Microparticles-2

A water dispersion of silicone elastomer microparticles was obtained in the same manner as production example 1, with the exceptions of altering the amount of the methylvinylpolysiloxane A1 from 350 g to 270 g, and replacing the 160 g of the methylhydrogenpolysiloxane B1 with 240 g of a methylhydrogenpolysiloxane B2 represented by formula (5) shown below and having a dimethylsiloxane unit content of 99.3 mol %, a molecular weight of 22,484 and a SiH group content of 0.018 mol/100 g (an amount equivalent to 1.07 SiH groups within the methylhydrogenpolysiloxane B2 per vinyl group within the methylvinylpolysiloxane A1). Inspection of the shape of these silicone elastomer microparticles in the same manner as production example 1 revealed spherical particles, and measurement of the volume average particle diameter of the silicone elastomer microparticles in the same manner as production example 1 yielded a result of 12 μm.

Using 882 g of the obtained water dispersion of silicone elastomer spherical microparticles as a raw material, a hydrolysis-condensation reaction and subsequent dewatering were conducted in the same manner as production example 1, thus forming microparticles with good flowability. During this process, the pH of the liquid upon addition of the 2,003 g of water and 57 g of 28% ammonia water was 11.2, and the amount of the polyorganosilsesquioxane following the hydrolysis-condensation reaction was 6.3 parts by mass per 100 parts by mass of the silicone elastomer spherical microparticles. Inspection of the obtained microparticles using an electron microscope revealed spherical particles, the surfaces of which were coated with particulate matter with a particle diameter of approximately 100 nm, confirming that silicone microparticles comprising the silicone elastomer spherical microparticles coated with a polyorganosilsesquioxane had been obtained. Dispersing the thus obtained silicone microparticles in water and subsequent measurement of the volume average particle diameter were conducted in the same manner as production example 1, yielding a result of 12 μm. The obtained silicone microparticles are referred to as Silicone microparticles-2.

With the exception of using the methylhydrogenpolysiloxane B2 instead of the methylhydrogenpolysiloxane B1, a non-sticky silicone elastomer was obtained in the same manner as production example 1. Measurement of the hardness of this silicone elastomer using a type A durometer meter prescribed in JIS K 6253 yielded a result of 20.

With the exception of using the methylhydrogenpolysiloxane B2 instead of the methylhydrogenpolysiloxane B1, preparation of a silicone elastomer sheet and measurement of the oil absorption amounts for the sheet were conducted in the same manner as production example 1. The oil absorption amounts listed in Table 1 represent absorption amounts per 1 g of the silicone elastomer.

The oil absorption amounts for 5.0 g of Silicone microparticles-2 were measured in the same manner as production example 1. Table 1 lists the oil absorption amounts, which were calculated using the formula: [mass (g) of solid fraction following solid-liquid separation]−5.0 (g).

$$HSiO(SiO)_{300}(SiO)_2SiH \quad (5)$$
with CH₃, H, CH₃ substituents

Production Example 3

Production of Silicone Microparticles-3

A water dispersion of silicone elastomer microparticles was obtained in the same manner as production example 1, with the exceptions of replacing the 350 g of the methylvinylpolysiloxane A1 with 170 g of a methylvinylpolysiloxane A2 represented by formula (6) shown below and having a dimethylsiloxane unit content of 98.9 mol %, a molecular weight of 13,696 and a vinyl group content of 0.029 mol/100 g, and replacing the 160 g of the methylhydrogenpolysiloxane B1 with 340 g of a methylhydrogenpolysiloxane B3 represented by formula (7) shown below and having a dimethylsiloxane unit content of 100 mol %, a molecular weight of 14,954 and a SiH group content of 0.013 mol/100 g (an amount equivalent to 0.90 SiH groups within the methylhydrogenpolysiloxane B3 per vinyl group within the methylvinylpolysiloxane A2). Inspection of the shape of these silicone elastomer microparticles in the same manner as production example 1 revealed spherical particles, and measurement of the volume average particle diameter of the silicone elastomer microparticles in the same manner as production example 1 yielded a result of 11 μm.

Using 882 g of the obtained water dispersion of silicone elastomer spherical microparticles as a raw material, a hydrolysis-condensation reaction and subsequent dewatering were conducted in the same manner as production example 1, thus forming microparticles with good flowability. During this process, the pH of the liquid upon addition of the 2,003 g of water and 57 g of 28% ammonia water was 11.2, and the amount of the polyorganosilsesquioxane following the hydrolysis-condensation reaction was 6.3 parts by mass per 100 parts by mass of the silicone elastomer spherical microparticles. Inspection of the obtained microparticles using an electron microscope revealed spherical particles, the surfaces of which were coated with particulate matter with a particle diameter of approximately 100 nm, confirming that silicone microparticles comprising the silicone elastomer spherical microparticles coated with a polyorganosilsesquioxane had been obtained. Dispersing the thus obtained silicone microparticles in water and subsequent measurement of the volume average particle diameter were conducted in the same manner as production example 1, yielding a result of 11 μm. The obtained silicone microparticles are referred to as Silicone microparticles-3.

With the exceptions of using the methylvinylpolysiloxane A2 instead of the methylvinylpolysiloxane A1, and using the methylhydrogenpolysiloxane B3 instead of the methylhydrogenpolysiloxane B1, a non-sticky silicone elastomer was obtained in the same manner as production example 1. Measurement of the hardness of this silicone elastomer using a type A durometer meter prescribed in JIS K 6253 yielded a result of 22.

With the exceptions of using the methylvinylpolysiloxane A2 instead of the methylvinylpolysiloxane A1, and using the methylhydrogenpolysiloxane B3 instead of the methylhydrogenpolysiloxane B1, preparation of a silicone elastomer sheet and measurement of the oil absorption amounts for the sheet were conducted in the same manner as production example 1. The oil absorption amounts listed in Table 1 represent absorption amounts per 1 g of the silicone elastomer.

The oil absorption amounts for 5.0 g of Silicone microparticles-3 were measured in the same manner as production example 1. Table 1 lists the oil absorption amounts, which were calculated using the formula: [mass (g) of solid fraction following solid-liquid separation]−5.0 (g).

(6)

(7)

Comparative Production Example 1

Production of Silicone Microparticles-4

A glass beaker with a capacity of 1 liter was charged with 500 g of the methylvinylpolysiloxane A1, and 19 g of a methylhydrogenpolysiloxane B4 represented by formula (8) shown below and having a dimethylsiloxane unit content of 75 mol %, a molecular weight of 2,393 and a SiH group content of 0.418 mol/100 g (an amount equivalent to 1.06 SiH groups within the methylhydrogenpolysiloxane B4 per vinyl group within the methylvinylpolysiloxane A1), and stirring and mixing were performed at 2,000 rpm using a homomixer. To the resulting mixed liquid were added 1.2 g of a polyoxyethylene lauryl ether (number of mols of added ethylene oxide=9 mol) and 100 g of water, and subsequent stirring at 6,000 rpm using the homomixer yielded an O/W type emulsion of increased viscosity. Stirring was continued for a further 15 minutes. Subsequently, with the stirring continued at 2,000 rpm, 377 g of water was added, yielding a uniform white emulsion. This emulsion was transferred to a glass flask with a capacity of 1 liter fitted with a stirring device having an anchor-shaped stirring blade, and following adjustment of the temperature to a value of 15 to 20° C., a mixed solution containing 0.8 g of a toluene solution of a chloroplatinic acid-olefin complex (platinum content: 0.5%) and 1.8 g of a polyoxyethylene lauryl ether (number of mols of added ethylene oxide=9 mol) was added to the flask under constant stirring. Stirring was then continued at the same temperature for 12 hours, thus forming a water dispersion of silicone elastomer microparticles. Inspection of the shape of these silicone elastomer microparticles under an optical microscope revealed that the particles were spherical, and measurement of the volume average particle diameter using a Multisizer 3 yielded a result of 12 μm.

1,155 g of the thus obtained water dispersion of silicone elastomer spherical microparticles was transferred to a glass flask with a capacity of 3 liters fitted with a stirring device having an anchor-shaped stirring blade, and 1,734 g of water and 60 g of 28% ammonia water were added to the flask. The pH of the liquid at this point was 11.3. Following lowering of the temperature to 5 to 10° C., 51 g of methyltrimethoxysilane (an amount that yields 4.2 parts by mass of a polymethylsilsesquioxane following the hydrolysis and condensation reaction per 100 parts by mass of the silicone elastomer spherical microparticles) was added dropwise to the flask over a period of 20 minutes, and stirring was then continued for a further 1 hour. During this period, the liquid temperature was maintained at 5 to 10° C. Subsequently, the reaction mixture was heated to 55 to 60° C., and stirring was continued at this temperature for 1 hour to complete the hydrolysis-condensation reaction of the methyltrimethoxysilane.

The obtained methyltrimethoxysilane hydrolysis-condensation reaction liquid was dewatered in the same manner as production example 1, yielding microparticles with good flowability. Inspection of these microparticles using an electron microscope revealed spherical particles, the surfaces of which were coated with particulate matter with a particle diameter of approximately 100 nm, confirming that silicone microparticles comprising the silicone elastomer spherical microparticles coated with a polyorganosilsesquioxane had been obtained. Dispersing the thus obtained silicone microparticles in water and subsequent measurement of the volume average particle diameter were conducted in the same manner as production example 1, yielding a result of 12 μm. The obtained silicone microparticles are referred to as Silicone microparticles-4.

With the exception of using the methylhydrogenpolysiloxane B4 instead of the methylhydrogenpolysiloxane B1, a non-sticky silicone elastomer was obtained in the same manner as production example 1. Measurement of the hardness of this silicone elastomer using a type A durometer prescribed in JIS K 6253 yielded a result of 29.

With the exception of using the methylhydrogenpolysiloxane B4 instead of the methylhydrogenpolysiloxane B1, preparation of a silicone elastomer sheet and measurement of the oil absorption amounts for the sheet were conducted in the same manner as production example 1. The oil absorption amounts listed in Table 1 represent absorption amounts per 1 g of the silicone elastomer.

The oil absorption amounts for 5.0 g of Silicone microparticles-4 were measured in the same manner as production example 1. Table 1 lists the oil absorption amounts, which were calculated using the formula: [mass (g) of solid fraction following solid-liquid separation]−5.0 (g).

(8)

Comparative Production Example 2

Production of Silicone Microparticles-5

A water dispersion of silicone elastomer microparticles was obtained in the same manner as comparative production example 1, with the exceptions of replacing the 19 g of the methylhydrogenpolysiloxane B4 with 17 g of a methylhydrogenpolysiloxane B5 represented by formula (9) shown below and having a dimethylsiloxane unit content of 66.7 mol %, a molecular weight of 10,577 and a SiH group content of 0.473 mol/100 g (an amount equivalent to 1.07 SiH groups within the methylhydrogenpolysiloxane B5 per vinyl group within the methylvinylpolysiloxane A1), and altering the amount of water added immediately prior to obtaining the uniform in white emulsion from 377 g to 379 g. Inspection of the shape of these silicone elastomer microparticles in the same manner as comparative production example 1 revealed spherical particles, and measurement of the volume average particle diameter of the silicone elastomer microparticles in the same manner as comparative production example 1 yielded a result of 12 μm.

With the exceptions of using 1,161 g of the obtained water dispersion of silicone elastomer spherical microparticles as a raw material, and altering the amount of water added from 1,734 g to 1,729 g, a hydrolysis-condensation reaction and subsequent dewatering were conducted in the same manner as comparative production example 1, thus forming microparticles with good flowability. During this process, the pH of the liquid upon addition of the 1,729 g of water and 60 g of 28% ammonia water was 11.3, and the amount of the polyorganosilsesquioxane following the hydrolysis-condensation reaction was 4.2 parts by mass per 100 parts by mass of the silicone elastomer spherical microparticles. Inspection of the obtained microparticles using an electron microscope revealed spherical particles, the surfaces of which were coated with particulate matter with a particle diameter of approximately 100 nm, confirming that silicone microparticles comprising the silicone elastomer spherical microparticles coated with a polyorganosilsesquioxane had been obtained. Dispersing the thus obtained silicone microparticles in water and subsequent measurement of the volume average particle diameter were conducted in the same manner as production example 1, yielding a result of 12 μm. The obtained silicone microparticles are referred to as Silicone microparticles-5.

With the exception of using the methylhydrogenpolysiloxane B5 instead of the methylhydrogenpolysiloxane B1, a non-sticky silicone elastomer was obtained in the same manner as production example 1. Measurement of the hardness of this silicone elastomer using a type A durometer prescribed in HS K 6253 yielded a result of 31.

With the exception of using the methylhydrogenpolysiloxane B5 instead of the methylhydrogenpolysiloxane B1, preparation of a silicone elastomer sheet and measurement of the oil absorption amounts for the sheet were conducted in the same manner as production example 1. The oil absorption amounts listed in Table 1 represent absorption amounts per 1 g of the silicone elastomer.

The oil absorption amounts for 5.0 g of Silicone microparticles-5 were measured in the same manner as production example 1. Table 1 lists the oil absorption amounts, which were calculated using the formula: [mass (g) of solid fraction following solid-liquid separation]−5.0 (g).

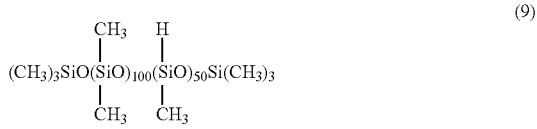
(9)

Comparative Production Example 3

Production of Silicone Microparticles-6

A water dispersion of silicone elastomer microparticles was obtained in the same manner as comparative production example 1, with the exceptions of replacing the 500 g of the methylvinylpolysiloxane A1 with 500 g of a methylvinylpolysiloxane A3 represented by formula (10) shown below and having a dimethylsiloxane unit content of 100 mol %, a molecular weight of 33,531 and a vinyl group content of 0.006 mol/100 g, altering the amount of the methylhydrogenpolysiloxane B4 from 19 g to 8 g (an amount equivalent to 1.11 SiH groups within the methylhydrogenpolysiloxane B4 per vinyl group within the methylvinylpolysiloxane A3), and altering the amount of water added immediately prior to obtaining the uniform white emulsion from 377 g to 388 g. Inspection of the shape of these silicone elastomer microparticles in the same manner as comparative production example 1 revealed spherical particles, and measurement of the volume average particle diameter of the silicone elastomer microparticles in the same manner as comparative production example 1 yielded a result of 13 μm.

With the exceptions of using 886 g of the obtained water dispersion of silicone elastomer spherical microparticles as a raw material, and altering the amount of water added from 2,003 g to 1,999 g, a hydrolysis-condensation reaction and subsequent dewatering were conducted in the same manner as production example 1, thus forming microparticles with good flowability. During this process, the pH of the liquid upon addition of the 1,999 g of water and 57 g of 28% ammonia water was 11.2, and the amount of the polyorganosilsesquioxane following the hydrolysis-condensation reaction was 6.3 parts by mass per 100 parts by mass of the silicone elastomer spherical microparticles. Inspection of the obtained microparticles using an electron microscope revealed spherical particles, the surfaces of which were coated with particulate matter with a particle diameter of approximately 100 nm, confirming that silicone microparticles comprising the silicone elastomer spherical microparticles coated with a polyorganosilsesquioxane had been obtained. Dispersing the thus obtained silicone microparticles in water and subsequent measurement of the volume average particle diameter were conducted in the same manner as production example 1, yielding a result of 13 μm. The obtained silicone microparticles are referred to as Silicone microparticles-6.

With the exceptions of using the methylvinylpolysiloxane A3 instead of the methylvinylpolysiloxane A1, and using the methylhydrogenpolysiloxane B4 instead of the methylhydrogenpolysiloxane B1, a non-sticky silicone elastomer was obtained in the same manner as production example 1. Measurement of the hardness of this silicone elastomer using a type A durometer prescribed in JIS K 6253 yielded a result of 21.

With the exceptions of using the methylvinylpolysiloxane A3 instead of the methylvinylpolysiloxane A1, and using the methylhydrogenpolysiloxane B4 instead of the methylhydrogenpolysiloxane B1, preparation of a silicone elastomer sheet and measurement of the oil absorption amounts for the sheet were conducted in the same manner as production example 1. The oil absorption amounts listed in Table 1 represent absorption amounts per 1 g of the silicone elastomer.

The oil absorption amounts for 5.0 g of Silicone microparticles-6 were measured in the same manner as production example 1. Table 1 lists the oil absorption amounts, which were calculated using the formula: [mass (g) of solid fraction following solid-liquid separation]−5.0 (g).

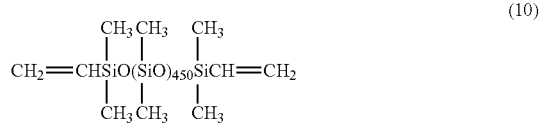
(10)

TABLE 1

Oil absorption amounts

| Item | | Production example | | | Comparative production example | | |
|---|---|---|---|---|---|---|---|
| | | 1 | 2 | 3 | 1 | 2 | 3 |
| Silicone elastomer oil absorption amount [g/1 g of silicone elastomer] | Decamethyl-cyclopentasiloxane (viscosity: 4.0 mm²/s) | 3.8 | 3.6 | 3.7 | 1.9 | 1.8 | 2.2 |
| | Dimethylpolysiloxane (viscosity: 6.0 mm²/s) | 2.4 | 2.4 | 2.5 | 1.2 | 1.1 | 1.5 |
| Silicone microparticles oil absorption amount [g/5 g of microparticles] | Decamethyl-cyclopentasiloxane (viscosity: 4.0 mm²/s) | 27 | 29 | 26 | 16 | 15 | 17 |
| | Dimethylpolysiloxane (viscosity: 6.0 mm²/s) | 20 | 22 | 20 | 10 | 9 | 12 |

From the results in Table 1 it has been evident that the silicone microparticles used in the present invention exhibited excellent absorption of silicone oils.

Examples 1 to 15 and Comparative Examples 1 to 15

Oily Gel Compositions

Using Silicone microparticles-1 obtained in the above production example 1, Silicone microparticles-2 obtained in the above production example 2, and Silicone microparticles-3 obtained in the above production example 3, oily gel compositions were prepared with the composition ratios (% by mass) listed in Table 2, and were then evaluated using the evaluation criteria shown in Table 4. On the other hand, using Silicone microparticles-4 obtained in the above comparative production example 1, Silicone microparticles-5 obtained in the above comparative production example 2, and Silicone microparticles-6 obtained in the above comparative production example 3, oily gel compositions were prepared with the composition ratios (% by mass) listed in Table 3, and were then evaluated using the evaluation criteria shown in Table 4. The evaluation results are listed in Table 5.

<Composition Ratios>

TABLE 2

Oily gel compositions comprising silicone microparticles obtained in the production examples

| No. | Component | Example | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| 1 | Silicone microparticles-1 | 25 | 25 | 25 | 25 | 40 | | | | | | | | | | |
| 2 | Silicone microparticles-2 | | | | | | 25 | 25 | 25 | 25 | 40 | | | | | |
| 3 | Silicone microparticles-3 | | | | | | | | | | | 25 | 25 | 25 | 25 | 40 |
| 4 | Decamethylcyclopentasiloxane | 75 | | | | | 75 | | | | | 75 | | | | |
| 5 | Methyl trimethicone | | 75 | | | | | 75 | | | | | 75 | | | |
| 6 | Octamethyltrisiloxane | | | 75 | | | | | 75 | | | | | 75 | | |
| 7 | Dimethylpolysiloxane (viscosity: 2 mm²/s) | | | | 75 | | | | | 75 | | | | | 75 | |
| 8 | Dimethylpolysiloxane (viscosity: 6 mm²/s) | | | | | 60 | | | | | 60 | | | | | 60 |

In the table, the numerical values represent composition ratios (% by mass)

TABLE 3

Oily gel compositions comprising silicone microparticles obtained in the comparative production examples

| No. | Component | Comparative Example | | | | | | | | | | | | | | |
|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| 1 | Silicone microparticles-4 | 25 | 25 | 25 | 25 | 40 | | | | | | | | | | |
| 2 | Silicone microparticles-5 | | | | | | 25 | 25 | 25 | 25 | 40 | | | | | |
| 3 | Silicone microparticles-6 | | | | | | | | | | | 25 | 25 | 25 | 25 | 40 |
| 4 | Decamethylcyclopentasiloxane | 75 | | | | | 75 | | | | | 75 | | | | |
| 5 | Methyl trimethicone | | 75 | | | | | 75 | | | | | 75 | | | |
| 6 | Octamethyltrisiloxane | | | 75 | | | | | 75 | | | | | 75 | | |
| 7 | Dimethylpolysiloxane (viscosity: 2 mm²/s) | | | | 75 | | | | | 75 | | | | | 75 | |

TABLE 3-continued

Oily gel compositions comprising silicone microparticles obtained in the comparative production examples

| No. | Component | Comparative Example |||||||||||||||
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| 8 | Dimethylpolysiloxane (viscosity: 6 mm²/s) | | | | | 60 | | | | | 60 | | | | | 60 |

In the table, the numerical values represent composition ratios (% by mass)

<Criteria for Evaluating Usability>

Each of the oily gel compositions was applied to the skin and evaluated for spreadability (malleability and ductility), oily film feeling (adhesion) and the state of powderiness (evaluated only for those compositions comprising a volatile oily component; describes the powdery sensation following evaporation of the oily component) by 10 expert panelists using the criteria outlined below in Table 4. The average number obtained was rated in accordance with the following criteria. The results are listed in Table 5.

TABLE 4

| Evaluation item | Spreadability | Oily film feeling upon application | Powderiness |
|---|---|---|---|
| 5 points | Good | Silky | Did not whiten |
| 4 points | Slightly good | Slightly silky | |
| 3 points | Fair | Fair | Whitened slightly |
| 2 points | Slightly poor | Slightly slimy | |
| 1 point | Poor | Slimy | Whitened |

Rating of Average Number of Points:

Obtained average number of points of 4.5 points or higher: ○○

Obtained average number of points of at least 3.5 points but less than 4.5 points: ○

Obtained average number of points of at least 2.5 points but less than 3.5 points: Δ

Obtained average number of points of at least 1.5 points but less than 2.5 points: X Obtained average number of points of less than 1.5 points: XX

TABLE 5

| Example | Rating ||| Comparative example | Rating |||
|---|---|---|---|---|---|---|---|
| | Spreadability | Oily film | Powderiness | | Spreadability | Oily film | Powderiness |
| 1 | ○○ | ○○ | ○○ | 1 | ○○ | Δ | ○○ |
| 2 | ○○ | ○○ | ○○ | 2 | ○○ | ○ | X |
| 3 | ○○ | ○○ | ○○ | 3 | ○○ | ○ | X |
| 4 | ○○ | ○○ | ○○ | 4 | ○○ | Δ | ○○ |
| 5 | ○○ | ○ | — | 5 | ○○ | X | — |
| 6 | ○○ | ○○ | ○○ | 6 | ○○ | Δ | ○○ |
| 7 | ○○ | ○○ | ○○ | 7 | ○○ | ○ | X |
| 8 | ○○ | ○○ | ○○ | 8 | ○○ | ○ | X |
| 9 | ○○ | ○○ | ○○ | 9 | ○○ | Δ | ○○ |
| 10 | ○○ | ○ | — | 10 | ○○ | X | — |
| 11 | ○○ | ○○ | ○○ | 11 | ○○ | Δ | ○○ |
| 12 | ○○ | ○○ | ○○ | 12 | ○○ | ○ | X |
| 13 | ○○ | ○○ | ○○ | 13 | ○○ | ○ | X |
| 14 | ○○ | ○○ | ○○ | 14 | ○○ | Δ | ○○ |
| 15 | ○○ | ○ | — | 15 | ○○ | X | — |

As is evident from Table 5, the compositions of examples 1 to 15 exhibited similar effects to the compositions of comparative examples 1 to 15 in terms of spreadability, but in terms of the oily film feeling upon application, the compositions of examples 1 to 15 were relatively less wet, and tended to impart a more silky feeling during use. The compositions of examples 1 to 15 also produced an esthetically pleasing finish following evaporation of the oily component, with no feeling of powderiness.

Examples 16 to 18, and Comparative Example 16

Skin Care Creams

Using Silicone microparticles-1 obtained in the above production example 1, Silicone microparticles-2 obtained in the above production example 2, Silicone microparticles-3 obtained in the above production example 3, and Silicone microparticles-6 obtained in the above comparative production example 3, skincare creams were prepared with the composition ratios (% by mass) listed in Table 6 below.

<Formulations>

TABLE 6

| Component | Composition (% by mass) | Example 16 | Example 17 | Example 18 | Comparative example 16 |
|---|---|---|---|---|---|
| 1 | Silicone microparticles-1 | 5.0 | — | — | — |
| 2 | Silicone microparticles-2 | — | 5.0 | — | — |
| 3 | Silicone microparticles-3 | — | — | 5.0 | — |
| 4 | Silicone microparticles-6 | — | — | — | 5.0 |
| 5 | Crosslinked polyether-modified silicone (note 1) | 3.0 | 3.0 | 3.0 | 3.0 |
| 6 | Crosslinked dimethylpolysiloxane (note 2) | 9.0 | 9.0 | 9.0 | 9.0 |
| 7 | Crosslinked dimethylpolysiloxane (note 3) | 22.0 | 22.0 | 22.0 | 22.0 |
| 8 | Polyether-modified branched silicone (note 4) | 1.0 | 1.0 | 1.0 | 1.0 |
| 9 | Decamethylcyclopentasiloxane | 25.0 | 25.0 | 25.0 | 25.0 |
| 10 | Liquid isoparaffin | 3.0 | 3.0 | 3.0 | 3.0 |
| 11 | 1,3-butylene glycol | 3.0 | 3.0 | 3.0 | 3.0 |
| 12 | Sodium citrate | 0.2 | 0.2 | 0.2 | 0.2 |
| 13 | Sodium chloride | 0.5 | 0.5 | 0.5 | 0.5 |
| 14 | Purified water | 28.3 | 28.3 | 28.3 | 28.3 |

(note 1) Crosslinked polyether-modified silicone: KSG-210 (manufactured by Shin-Etsu Chemical Co., Ltd.)
(note 2) Crosslinked dimethylpolysiloxane: KSG-15 (manufactured by Shin-Etsu Chemical Co., Ltd.)
(note 3) Crosslinked dimethylpolysiloxane: KSG-16 (manufactured by Shin-Etsu Chemical Co., Ltd.)
(note 4) Polyether-modified branched silicone: KF-6028 (manufactured by Shin-Etsu Chemical Co., Ltd.)

<Preparation of Cosmetics>

The components 1 to 10 were stirred and mixed in a beaker. To the resulting mixture was added a solution obtained separately by dissolving the components 11 to 13 in the component 14, and stirring was then continued to complete preparation of a skincare cream. The obtained skincare cream was subjected to the evaluations described below.

<Evaluation of Usability and Feeling During Use>

Each skincare cream was applied to the skin and evaluated for spreadability (malleability and ductility), skin affinity (adhesion and homogeneity) and residual oily film feeling on the skin (sensation following application) by 20 expert female panelists using the criteria outlined below in Table 7. The average number obtained was rated in accordance with the following criteria. The results are listed in Table 8.

TABLE 7

| Item | Spreadability | Skin affinity | Residual oily film feeling on skin |
|---|---|---|---|
| 5 points | Light | Good | Silky |
| 4 points | Slightly light | Slightly good | Slightly silky |
| 3 points | Fair | Fair | Fair |
| 2 points | Slightly heavy | Slightly poor | Slightly slimy |
| 1 point | Heavy | Poor | Slimy |

Rating of Average Number of Points:

Obtained average number of points of 4.5 points or higher: ⊚

Obtained average number of points of at least 3.5 points but less than 4.5 points: ○

Obtained average number of points of at least 2.5 points but less than 3.5 points: Δ

Obtained average number of points of at least 1.5 points but less than 2.5 points: X Obtained average number of points of less than 1.5 points: XX

TABLE 8

| Item | Example 16 | Example 17 | Example 18 | Comparative example 16 |
|---|---|---|---|---|
| Spreadability | ⊚ | ⊚ | ⊚ | XX |
| Skin affinity | ⊚ | ⊚ | ⊚ | ⊚ |
| Residual oil film feeling on skin | ⊚ | ⊚ | ⊚ | X |

As is evident from Table 8, it was demonstrated that the skincare creams of examples 16 to 18 exhibited superior levels of usability compared with the skincare cream of comparative example 16. In other words, it was clear that by including the silicone microparticles used in the present invention, a cosmetic could be obtained that exhibited no stickiness upon application, had excellent spreadability and adhesion, and left no unpleasant residual oily film feeling on the skin following application.

Example 19

Powder Foundation

| Components | mass (%) |
|---|---|
| 1. Liquid paraffin | 2.0 |
| 2. Squalane | 2.0 |
| 3. Dimethylpolysiloxane (viscosity: 20 mm$^2$/s) | 3.0 |

-continued

| Components | mass (%) |
|---|---|
| 4. Polyethylene | 1.5 |
| 5. Methylhydrogenpolysiloxane-treated mica | 40.0 |
| 6. Barium sulfate | 5.0 |
| 7. Metal soap-treated titanium oxide | 9.0 |
| 8. Silicone microparticles-1 | 6.0 |
| 9. Methylhydrogenpolysiloxane-treated talc | 31.5 |
| 10. Triethoxysilylethyl polydimethylsiloxyethyl hexyl dimethicone (note 1)-treated iron oxide pigment | appropriate amount |

(note 1) Triethoxysilylethyl polydimethylsiloxyethyl hexyl dimethicone: KF-9909 (manufactured by Shin-Etsu Chemical Co., Ltd.)

(Production Method)

A: Components 4 to 10 were placed in a Henschel mixer and mixed thoroughly.

B: Components 1 to 3 were heated and dissolved, and the resulting solution was added to the mixture obtained in A and mixed thoroughly.

C: The resulting mixture was crushed using a hammer mill, and press-molded into a predetermined aluminum pan, yielding a powder foundation.

The powder foundation obtained in this manner was confirmed as having a fine texture, ready spreadability, and no stickiness or greasiness, as well as offering excellent cosmetic retention properties.

Example 20

Oil-in-Water Cream

| Components | mass (%) |
|---|---|
| 1. Crosslinked dimethylpolysiloxane (note 1) | 10.0 |
| 2. Glyceryl trioctanoate | 5.0 |
| 3. Silicone microparticles-2 | 1.0 |
| 4. Dipropylene glycol | 7.0 |
| 5. Glycerol | 5.0 |
| 6. Methyl cellulose (2% aqueous solution) (note 2) | 7.0 |
| 7. Polyacrylamide-based emulsifier (note 3) | 2.0 |
| 8. Preservative | appropriate amount |
| 9. Fragrance | appropriate amount |
| 10. Pure water | remainder |

(note 1) Crosslinked dimethylpolysiloxane: KSG-16 (manufactured by Shin-Etsu Chemical Co., Ltd.)
(note 2) Methyl cellulose: Metolose SM-4000 (manufactured by Shin-Etsu Chemical Co., Ltd.)
(note 3) Polyacrylamide-based emulsifier: Sepigel 305 (manufactured by Seppic Corporation)

(Production Method)

A: Components 4 to 10 were mixed.

B: Components 1 to 3 were mixed, and the resulting mixture was added to the mixture obtained in A and then stirred and emulsified.

The oil-in-water cream obtained in this manner was confirmed as having a fine texture, ready spreadability, and no stickiness or greasiness, as well as offering excellent stability, with no change upon temperature variation and no change over time.

Example 21

Water-in-Oil Cream

| Components | mass (%) |
|---|---|
| 1. Dimethylpolysiloxane (viscosity: 6 mm$^2$/s) | 6.0 |
| 2. Methylphenylpolysiloxane | 4.0 |
| 3. Squalane | 5.0 |
| 4. Neopentyl glycol dioctanoate | 3.0 |
| 5. Polyether-modified silicone (note 1) | 3.0 |
| 6. Silicone microparticles-3 | 2.0 |
| 7. Glycerol | 10.0 |
| 8. Preservative | appropriate amount |
| 9. Fragrance | appropriate amount |
| 10. Pure water | remainder |

(note 1) Polyether-modified silicone: KF-6012 (manufactured by Shin-Etsu Chemical Co., Ltd.)

(Production Method)

A: Components 1 to 6 were mixed uniformly.

B: Components 7, 8 and 10 were mixed and dissolved.

C: Under constant stirring, the mixture obtained in B was added to the mixture obtained in A, and following emulsification, the component 9 was added to complete preparation of a cream.

The water-in-oil cream obtained in this manner was confirmed as having a fine texture, ready spreadability, and no stickiness or greasiness, as well as offering excellent stability, with no change upon temperature variation and no change over time.

Example 22

Water-in-Oil Cream

| Components | mass (%) |
|---|---|
| 1. Alkyl-modified crosslinked polyether-modified silicone (note 1) | 6.0 |
| 2. Liquid paraffin | 13.5 |
| 3. *Macadamia* nut oil | 5.0 |
| 4. Alkylsilicone/polyether-comodified silicone (note 2) | 0.5 |
| 5. Hybrid silicone complex powder (note 3) | 3.0 |
| 6. Silicone microparticles-1 | 2.0 |
| 7. Sodium citrate | 0.2 |
| 8. Propylene glycol | 8.0 |
| 9. Glycerol | 3.0 |
| 10. Preservative | appropriate amount |
| 11. Fragrance | appropriate amount |
| 12. Pure water | remainder |

(note 1) Alkyl-modified crosslinked polyether-modified silicone: KSG-310 (manufactured by Shin-Etsu Chemical Co., Ltd.)
(note 2) Alkylsilicone/polyether-comodified silicone: KF-6038 (manufactured by Shin-Etsu Chemical Co., Ltd.)
(note 3) Hybrid silicone complex powder: KSP-100 (manufactured by Shin-Etsu Chemical Co., Ltd.)

(Production Method)

A: Components 1 to 6 were mixed.

B: Components 7 to 10 and component 12 were mixed and dissolved.

C: Under constant stirring, the mixture obtained in B was added to the mixture obtained in A, and following emulsification, the component 11 was added to complete preparation of a cream.

The water-in-oil cream obtained in this manner was confirmed as having a fine texture, ready spreadability, and no stickiness or greasiness, as well as offering excellent stability, with no change upon temperature variation and no change over time.

Example 23

Water-in-Oil Cream

| Components | mass (%) |
|---|---|
| 1. Decamethylcyclopentasiloxane | 10.5 |
| 2. Dimethylpolysiloxane (viscosity: 6 mm$^2$/s) | 4.0 |
| 3. Polyether-modified silicone (note 1) | 5.0 |
| 4. POE (5) octyl dodecyl ether | 1.0 |
| 5. Polyoxyethylene sorbitan monostearate (20 E.O.) | 0.5 |
| 6. The gel composition of example 1 | 15.0 |
| 7. Liquid paraffin | 2.0 |
| 8. *Macadamia* nut oil | 1.0 |
| 9. *Scutellaria Baicalensis* root extract (note 2) | 1.0 |
| 10. *Gentiana* extract (note 3) | 0.5 |
| 11. Ethanol | 5.0 |
| 12. 1,3-butylene glycol | 2.0 |
| 13. Preservative | appropriate amount |
| 14. Fragrance | appropriate amount |
| 15. Pure water | remainder |

(note 1) Polyether-modified silicone: KF-6017 (manufactured by Shin-Etsu Chemical Co., Ltd.)
(note 2) *Scutellaria Baicalensis* root extract: 50% extract in 1,3-butylene glycol water
(note 3) *Gentiana* extract: 20% extract in ethanol water (Production Method)
A: Components 1 to 8 were mixed and dispersed uniformly.
B: Components 9 to 13 and component 15 were mixed, and the mixture obtained in A was then added and emulsified.
C: Component 14 was added to the mixture obtained in B to complete preparation of a cream.

The water-in-oil cream obtained in this manner was confirmed as not only having a fine texture and no stickiness, but also offering excellent spreadability and adhesion, and exhibiting extremely superior cosmetic retention. Further, the cream also exhibited excellent stability, with no change by temperature and no change over time.

Example 24

Eye Liner

| Components | mass (%) |
|---|---|
| 1. Decamethylcyclopentasiloxane | 39.0 |
| 2. Polyether-modified silicone (note 1) | 3.0 |
| 3. Organic silicone resin (note 2) | 15.0 |
| 4. Dioctadecyldimethylammonium salt-modified montmorillonite | 3.0 |
| 5. Methylhydrogenpolysiloxane-treated iron oxide black | 8.0 |
| 6. Silicone microparticles-2 | 2.0 |
| 7. 1,3-butylene glycol | 5.0 |
| 8. Sodium dehydroacetate | appropriate amount |
| 9. Preservative | appropriate amount |
| 10. Pure water | remainder |

(note 1) Polyether-modified silicone: KF-6017 (manufactured by Shin-Etsu Chemical Co., Ltd.)
(note 2) Organic silicone resin: KF-7312J (manufactured by Shin-Etsu Chemical Co., Ltd.)

(Production Method)
A: Components 1 to 4 were mixed, and components 5 and 6 were then added and dispersed uniformly.
B: Components 7 to 10 were mixed.
C: The mixture obtained in B was added gradually to the mixture obtained in A and emulsified, thus completing preparation of an eye liner.

The eye liner obtained in this manner was readily spread and easy to draw, yielded a cool and fresh sensation, and exhibited superior feelings during use with no stickiness. Further, the eye liner also exhibited excellent usability and stability, with no change upon temperature variation and no change over time, exhibited excellent water resistance and sweat resistance, and also offered extremely favorable cosmetic retention.

Example 25

Foundation

| Components | mass (%) |
|---|---|
| 1. Decamethylcyclopentasiloxane | 45.0 |
| 2. Dimethylpolysiloxane (viscosity: 6 mm$^2$/s) | 15.0 |
| 3. Polyether-modified silicone (note 1) | 3.5 |
| 4. Octadecyldimethylbenzylammonium salt-modified montmorillonite | 1.5 |
| 5. Silicone microparticles-3 | 4.5 |
| 6. Amino acid (N-acylglutamic acid)-treated iron oxide | 2.5 |
| 7. Triethoxysilylethyl polydimethylsiloxyethyl hexyl dimethicone (note 2)-treated titanium oxide | 7.5 |
| 8. Dipropylene glycol | 5.0 |
| 9. Methyl paraoxybenzoate | 0.3 |
| 10. Fragrance | appropriate amount |
| 11. Pure water | remainder |

(note 1) Polyether-modified silicone: KF-6017 (manufactured by Shin-Etsu Chemical Co., Ltd.)
(note 2) Triethoxysilylethyl polydimethylsiloxyethyl hexyl dimethicone: KF-9909 (manufactured by Shin-Etsu Chemical Co., Ltd.)

(Production Method)
A: Components 1 to 4 were mixed, and components 5 to 7 were added and mixed uniformly.
B: Components 8, 9 and 11 were dissolved.
C: Under constant stirring, the mixture obtained in B was added to the mixture obtained in A, and following emulsification, the component 10 was added to complete preparation of a foundation.

The foundation obtained in this manner was confirmed as having a fine texture, ready spreadability, no stickiness or greasiness, and favorable cosmetic retention, as well as offering excellent stability, with no change upon temperature variation and no change over time.

Example 26

Eye Shadow

| Components | mass (%) |
|---|---|
| 1. Decamethylcyclopentasiloxane | 15.0 |
| 2. Dimethylpolysiloxane (viscosity: 6 mm$^2$/s) | 10.0 |
| 3. Polyether-modified branched silicone (note 1) | 2.0 |
| 4. PEG (10) lauryl ether | 0.5 |

-continued

| Components | mass (%) |
|---|---|
| 5. Silicone microparticles-1 | 6.0 |
| 6. Methylhydrogenpolysiloxane-treated inorganic coloring pigment | appropriate amount |
| 7. Sodium chloride | 2.0 |
| 8. Propylene glycol | 8.0 |
| 9. Preservative | appropriate amount |
| 10. Fragrance | appropriate amount |
| 11. Pure water | remainder |

(note 1) Polyether-modified branched silicone: KF-6028 (manufactured by Shin-Etsu Chemical Co., Ltd.)

(Production Method)

A: Components 1 to 4 were mixed, and components 5 and 6 were added and dispersed uniformly.

B: Components 7 to 9 and component 11 were dissolved uniformly.

C: Under constant stirring, the mixture obtained in B was added to the mixture obtained in A, and following emulsification, the component 10 was added to complete preparation of an eye shadow.

The eye shadow obtained in this manner exhibited ready spreadability and favorable feelings during use, with no greasiness or powderiness. Further, the water resistance, water repellency and sweat resistance were good, retention was favorable with good resistance to cosmetic breakdown, and the eye shadow also exhibited excellent stability, with no change upon temperature variation and no change over time.

Example 27

Lipstick

| Components | mass (%) |
|---|---|
| 1. Candelilla wax | 8.0 |
| 2. Polyethylene wax | 8.0 |
| 3. Long-chain alkyl-containing acrylic silicone resin (note 1) | 12.0 |
| 4. Methylphenylpolysiloxane (note 2) | 3.0 |
| 5. Isotridecyl isononanoate | 20.0 |
| 6. Glyceryl isostearate | 16.0 |
| 7. Polyglyceryl triisostearate | 28.5 |
| 8. Silicone microparticles-2 | 1.5 |
| 9. Organic pigment | appropriate amount |
| 10. Fragrance | appropriate amount |

(note 1) Long-chain alkyl-containing acrylic silicone resin: KP-561P (manufactured by Shin-Etsu Chemical Co., Ltd.)
(note 2) Methylphenylpolysiloxane: KF-54 (manufactured by Shin-Etsu Chemical Co., Ltd.)

(Production Method)

A: Components 1 to 6 and a portion of component 7 were mixed and dissolved under heat.

B: Components 8 and 9 and the remainder of component 7 were mixed uniformly, and the resulting mixture was added to the mixture obtained in A and dispersed uniformly.

C: The component 10 was added to the mixture obtained in B to complete preparation of a lipstick.

The lipstick obtained in this manner exhibited ready spreadability, suffered no greasiness or powderiness, exhibited favorable water resistance and water repellency, offered good cosmetic retention, and also exhibited excellent stability.

Example 28

Eye Liner

| Components | mass (%) |
|---|---|
| 1. Decamethylcyclopentasiloxane | 6.0 |
| 2. Dimethylpolysiloxane (viscosity: 6 mm$^2$/s) | 5.0 |
| 3. Jojoba oil | 2.0 |
| 4. Polyether-modified silicone (note 1) | 1.0 |
| 5. Alkylsilicone/polyether-comodified silicone (note 2) | 1.0 |
| 6. Acrylic silicone resin (note 3) | 15.0 |
| 7. Silicone microparticles-1 | 2.0 |
| 8. Methylhydrogenpolysiloxane-treated iron oxide black | 18.0 |
| 9. Ethanol | 5.0 |
| 10. Preservative | appropriate amount |
| 11. Pure water | remainder |

(note 1) Polyether-modified silicone: KF-6017 (manufactured by Shin-Etsu Chemical Co., Ltd.)
(note 2) Alkylsilicone/polyether-comodified silicone: KF-6038 (manufactured by Shin-Etsu Chemical Co., Ltd.)
(note 3) Acrylic silicone resin: KP-545 (manufactured by Shin-Etsu Chemical Co., Ltd.)

(Production Method)

A: Components 1 to 6 were mixed, and components 7 and 8 were then added and dispersed uniformly.

B: Components 9 to 11 were stirred and dissolved.

C: Under constant stirring, the mixture obtained in B was added to the mixture obtained in A and emulsified, thus completing preparation of an eye liner.

The eye liner obtained in this manner was readily spread, suffered no greasiness or powderiness, exhibited favorable water resistance, water repellency and sweat resistance, offered good cosmetic retention, and was resistant to cosmetic breakdown. Further, the eye liner was also confirmed as having excellent stability, with no change upon temperature variation and no change over time.

Example 29

Liquid Emulsified Foundation

| Components | mass (%) |
|---|---|
| 1. Dimethylpolysiloxane (viscosity: 6 mm$^2$/s) | 4.5 |
| 2. Decamethylcyclopentasiloxane | 10.0 |
| 3. Squalane | 4.0 |
| 4. Neopentyl glycol dioctanoate | 3.0 |
| 5. Isostearic acid diglyceride | 2.0 |
| 6. α-monoisostearyl glyceryl ether | 1.0 |
| 7. Polyether-modified silicone (note 1) | 1.0 |
| 8. Alkylsilicone/polyether-comodified silicone (note 2) | 0.5 |
| 9. Aluminum distearate | 0.2 |
| 10. The gel composition from example 6 | 9.0 |
| 11. Methylhydrogenpolysiloxane-treated iron oxide pigment | appropriate amount |
| 12. Glycerol | 3.0 |
| 13. Preservative | appropriate amount |

-continued

| Components | mass (%) |
| --- | --- |
| 14. Fragrance | appropriate amount |
| 15. Pure water | remainder |

(note 1) Polyether-modified silicone: KF-6017 (manufactured by Shin-Etsu Chemical Co., Ltd.)
(note 2) Alkylsilicone/polyether-comodified silicone: KF-6038 (manufactured by Shin-Etsu Chemical Co., Ltd.)

(Production Method)

A: Components 1 to 9 were mixed under heat, and components 10 and 11 were then added and dispersed uniformly.

B: Components 12, 13 and 15 were heated and dissolved.

C: Under constant stirring, the mixture obtained in B was added to the mixture obtained in A and emulsified, and following cooling, the component 14 was added to complete preparation of a liquid emulsified foundation.

The liquid emulsified foundation obtained in this manner was confirmed as having a low viscosity and fine texture, ready spreadability with no stickiness or greasiness, and a favorable skin corrective effect, as well as offering favorable cosmetic retention and excellent stability, with no change upon temperature variation and no change over time.

Example 30

Liquid Foundation

| Components | mass (%) |
| --- | --- |
| 1. Decamethylcyclopentasiloxane | 16.0 |
| 2. Dimethylpolysiloxane (viscosity: 6 mm$^2$/s) | 8.0 |
| 3. Octyl para-methoxycinnamate | 3.0 |
| 4. 12-hydroxystearic acid | 1.0 |
| 5. Fluorine-modified silicone (note 1) | 15.0 |
| 6. Fluoroalkyl/polyether-comodified silicone (note 2) | 5.0 |
| 7. Spherical polymethylsilsesquioxane powder (note 3) | 1.0 |
| 8. Silicone microparticles-1 | 3.0 |
| 9. Silicone microparticles-4 | 3.0 |
| 10. Amino acid (N-acylglutamic acid)-treated iron oxide pigment | appropriate amount |
| 11. Ethanol | 15.0 |
| 12. Glycerol | 3.0 |
| 13. Magnesium sulfate | 1.0 |
| 14. Preservative | appropriate amount |
| 15. Fragrance | appropriate amount |
| 16. Pure water | remainder |

(note 1) Fluorine-modified silicone: FL-50 (manufactured by Shin-Etsu Chemical Co., Ltd.)
(note 2) Fluoroalkyl/polyether-comodified silicone: FPD-4694 (manufactured by Shin-Etsu Chemical Co., Ltd.)
(note 3) Spherical polymethylsilsesquioxane powder: KMP-590 (manufactured by Shin-Etsu Chemical Co., Ltd.)

(Production Method)

A: Components 7 to 10 were mixed together uniformly.

B: Components 1 to 6 were mixed under heating at 70° C., and the mixture obtained in A was then added and dispersed uniformly.

C: Components 11 to 14 and component 16 were heated to 40° C., the mixture obtained in B was added and emulsified, and following cooling, the component 15 was added to complete preparation of a liquid foundation.

The liquid foundation obtained in this manner was confirmed as suffering no stickiness, having favorable spreadability, and offering excellent stability, with no change upon temperature variation and no change over time.

Example 31

Eye Liner

| Components | mass (%) |
| --- | --- |
| 1. Decamethylcyclopentasiloxane | 22.0 |
| 2. Dimethylpolysiloxane (viscosity: 6 mm$^2$/s) | 2.0 |
| 3. Methylhydrogenpolysiloxane-treated iron oxide black | 20.0 |
| 4. The gel composition of example 15 | 4.0 |
| 5. Organic silicone resin (note 1) | 10.0 |
| 6. Vitamin E acetate | 0.2 |
| 7. Jojoba oil | 2.0 |
| 8. Bentonite | 3.0 |
| 9. Polyether-modified silicone (note 2) | 2.0 |
| 10. Ethanol | 3.0 |
| 11. 1,3-butylene glycol | 5.0 |
| 12. Preservative | appropriate amount |
| 13. Pure water | remainder |

(note 1) Organic silicone resin: KF-7312J (manufactured by Shin-Etsu Chemical Co., Ltd.)
(note 2) Polyether-modified silicone: KF-6017 (manufactured by Shin-Etsu Chemical Co., Ltd.)

(Production Method)

A: Components 1, 2 and 5 to 9 were mixed, and components 3 and 4 were then added and dispersed uniformly.

B: Components 10 to 13 were mixed.

C: Under constant stirring, the mixture obtained in B was added gradually to the mixture obtained in A and emulsified, thus completing preparation of an eye liner.

The eye liner obtained in this manner was readily spread and easy to draw, yielded a cool and fresh sensation, exhibited superior feelings during use with no stickiness, offered excellent water resistance and sweat resistance, and also provided excellent cosmetic retention. Further, the eye liner suffered no change by temperature and no change over time.

Example 32

Foundation

| Components | mass (%) |
| --- | --- |
| 1. Decamethylcyclopentasiloxane | 15.0 |
| 2. Methylphenylpolysiloxane | 3.0 |
| 3. Glyceryl trioctanoate | 10.0 |
| 4. Polyether-modified silicone (note 1) | 4.0 |
| 5. Polyglyceryl monoisostearate | 3.0 |
| 6. The gel composition of example 6 | 15.0 |
| 7. Aluminum stearate-treated titanium oxide | 6.0 |
| 8. Methylhydrogenpolysiloxane-treated iron oxide pigment | appropriate amount |
| 9. 1,3-butylene glycol | 7.0 |
| 10. Sodium chloride | 0.5 |
| 11. Preservative | appropriate amount |
| 12. Fragrance | appropriate amount |
| 13. Pure water | remainder |

(note 1) Polyether-modified silicone: KF-6017 (manufactured by Shin-Etsu Chemical Co., Ltd.)

(Production Method)

A: Components 1 to 5 were mixed and dissolved, and components 6 to 8 were then dispersed uniformly therein.

B: Components 9 to 11 and component 13 were mixed and then added to the mixture obtained in A and emulsified.

C: Component 12 was added to the mixture obtained in B to complete preparation of a foundation.

The foundation obtained in this manner was confirmed as having no stickiness, ready spreadability, an excellent feeling of adhesion and superior retention. Further, the foundation also exhibited excellent stability, with no change by temperature and no change over time.

Example 33

Water-in-Oil Antiperspirant

| Components | mass (%) |
|---|---|
| 1. Crosslinked polyether-modified silicone (note 1) | 7.0 |
| 2. Decamethylcyclopentasiloxane | 10.0 |
| 3. Glyceryl trioctanoate | 7.0 |
| 4. Dipropylene glycol | 5.0 |
| 5. Sodium citrate | 0.2 |
| 6. Aluminum zirconium tetrachlorohydrate | 18.0 |
| 7. Silicone microparticles-2 | 5.0 |
| 8. Fluorine-modified hybrid silicone complex powder (note 2) | 2.0 |
| 9. Fragrance | appropriate amount |
| 10. Pure water | 45.8 |

(note 1) Crosslinked polyether-modified silicone: KSG-210 (manufactured by Shin-Etsu Chemical Co., Ltd.)
(note 2) Fluorine-modified hybrid silicone complex powder: KSP-200 (manufactured by Shin-Etsu Chemical Co., Ltd.)

(Production Method)

A: Components 1 to 3 were mixed.
B: Components 4 to 10 were mixed.
C: The mixture obtained in B was added to the mixture obtained in A, and the resulting mixture was emulsified.

The water-in-oil antiperspirant obtained in this manner exhibited good spreadability and no stickiness or oily feeling, and also displayed extremely superior usability and stability, with no change by temperature and no change over time.

Example 34

Roll-On Antiperspirant

| | Components | mass (%) |
|---|---|---|
| 1. | Crosslinked polyether-modified silicone (note 1) | 20.0 |
| 2. | Dimethylpolysiloxane (viscosity: 6 mm²/s) | 10.0 |
| 3. | Crosslinked dimethylpolysiloxane (note 2) | 15.0 |
| 4. | Decamethylcyclopentasiloxane | 15.0 |
| 5. | Aluminum zirconium tetrachlorohydrate | 20.0 |
| 6. | The gel composition of example 11 | 20.0 |
| 7. | Fragrance | appropriate amount |

(note 1) Crosslinked polyether-modified silicone: KSG-210 (manufactured by Shin-Etsu Chemical Co., Ltd.)
(note 2) Crosslinked dimethylpolysiloxane: KSG-15 (manufactured by Shin-Etsu Chemical Co., Ltd.)

(Production Method)

A: Components 1 to 4 were mixed.
B: Components 5 to 7 were added to the mixture obtained in A and dispersed uniformly.

The roll-on antiperspirant obtained in this manner exhibited good spreadability and no stickiness or oily feeling, and also displayed extremely superior usability and stability, with no change by temperature and no change over time.

Example 35

Sunblock Lotion

| Components | mass (%) |
|---|---|
| 1. Decamethylcyclopentasiloxane | 20.0 |
| 2. Methylphenylpolysiloxane | 3.0 |
| 3. Sorbitan monoisostearate | 1.0 |
| 4. Polyether-modified silicone (note 1) | 0.5 |
| 5. Trimethylsiloxysilicate (note 2) | 1.0 |
| 6. Octyl para-methoxycinnamate | 4.0 |
| 7. Silicone microparticles-3 | 2.0 |
| 8. Aluminum stearate-treated titanium oxide microparticles | 6.0 |
| 9. Sorbitol | 2.0 |
| 10. Sodium chloride | 2.0 |
| 11. Preservative | appropriate amount |
| 12. Fragrance | appropriate amount |
| 13. Pure water | remainder |

(note 1) Polyether-modified silicone: KF-6015 (manufactured by Shin-Etsu Chemical Co., Ltd.)
(note 2) Trimethylsiloxysilicate: X-21-5250 (manufactured by Shin-Etsu Chemical Co., Ltd.)

(Production Method)

A: Components 1 to 6 were mixed under heat, and components 7 and 8 were then dispersed uniformly therein.
B: Components 9 to 11 and component 13 were mixed under heat.
C: Under constant stirring, the mixture obtained in B was added gradually to the mixture obtained in A and emulsified, and following cooling, component 12 was added to complete the preparation of a sunblock lotion.

The sunblock lotion obtained in this manner had a fine texture, exhibited ready spreadability, and suffered no stickiness. Moreover, the cosmetic retention was good, meaning the ultraviolet blocking effect was favorably retained, and the lotion also exhibited excellent stability, with no change upon temperature variation and no change over time.

Example 36

Sunblock Cream

| Components | mass (%) |
|---|---|
| 1. Decamethylcyclopentasiloxane | 11.5 |
| 2. Acrylic silicone resin (note 1) | 12.0 |
| 3. Glyceryl trioctanoate | 5.0 |
| 4. Octyl para-methoxycinnamate | 6.0 |
| 5. Crosslinked polyether-modified silicone (note 2) | 5.0 |
| 6. Alkylsilicone/polyether-comodified silicone (note 3) | 2.5 |
| 7. The gel composition of example 4 | 8.0 |
| 8. Aluminum stearate-treated titanium oxide microparticles | 15.0 |
| 9. Sodium chloride | 0.5 |
| 10. 1,3-butylene glycol | 2.0 |
| 11. Preservative | appropriate amount |

-continued

| Components | mass (%) |
|---|---|
| 12. Fragrance | appropriate amount |
| 13. Pure water | remainder |

(note 1) Acrylic silicone resin: KP-545 (manufactured by Shin-Etsu Chemical Co., Ltd.)
(note 2) Crosslinked polyether-modified silicone: KSG-210 (manufactured by Shin-Etsu Chemical Co., Ltd.)
(note 3) Alkylsilicone/polyether-comodified silicone: KF-6038 (manufactured by Shin-Etsu Chemical Co., Ltd.)

(Production Method)

A: Component 2 was added to a portion of component 1 and mixed uniformly, and component 8 was then added and dispersed using a beads mill.

B: The remainder of component 1 and components 3 to 7 were mixed together uniformly.

C: Components 9 to 11 and component 13 were mixed and dissolved.

D: The mixture obtained in C was added to the mixture obtained in B and emulsified, the mixture obtained in A was then added and dispersed, and component 12 was then added to complete preparation of a sunblock cream.

The sunblock cream obtained in this manner suffered no stickiness, exhibited good spreadability and an excellent feeling of adhesion, displayed a skin corrective effect, and also exhibited excellent cosmetic retention. Further, the cream was also confirmed as having excellent stability, with no change upon temperature variation and no change over time.

Example 37

Nail Enamel

| Components | mass (%) |
|---|---|
| 1. Acrylic silicone resin (note 1) | 45.0 |
| 2. Methyl trimethicone (note 2) | 5.0 |
| 3. Nitrocellulose | 3.0 |
| 4. Camphor | 0.5 |
| 5. Acetyltributyl citrate | 1.0 |
| 6. Dimethyldistearylammonium hectorite | 0.5 |
| 7. Butyl acetate | 30.0 |
| 8. Ethyl acetate | 10.0 |
| 9. Isopropyl alcohol | 5.0 |
| 10. Silicone microparticles-3 | appropriate amount |

(note 1) Acrylic silicone resin: KP-549 (manufactured by Shin-Etsu Chemical Co., Ltd.)
(note 2) Methyl trimethicone: TMF-1.5 (manufactured by Shin-Etsu Chemical (Production Method)

A: Components 7 to 9 were mixed, and components 4 to 6 were then added and mixed uniformly therein.

B: Components 1 to 3 were added to the mixture obtained in A and mixed thoroughly.

C: Component 10 was added to the mixture obtained in B and mixed thoroughly, yielding a nail enamel.

The nail enamel obtained in this manner exhibited ready spreadability, produced a smooth look, exhibited favorable water resistance, oil resistance and retention, and displayed excellent stability, with no sensation of pressure on the nails, no yellowing of the nails, and no change in the cosmetic film by temperature or over time.

Example 38

Cheek Colorant

| Components | mass (%) |
|---|---|
| 1. Crosslinked dimethylpolysiloxane (note 1) | 28.0 |
| 2. Decamethylcyclopentasiloxane | 34.5 |
| 3. Neopentyl glycol dioctanoate | 9.0 |
| 4. Stearoyl inulin | 10.0 |
| 5. Silicone microparticles-1 | 2.0 |
| 6. Red No. 202 | appropriate amount |
| 7. Alkylsilicone branched silicone (note 2)-treated iron oxide | appropriate amount |
| 8. Alkylsilicone branched silicone (note 2)-treated titanium oxide | appropriate amount |
| 9. Tocopherol | appropriate amount |
| 10. Alkylsilicone branched silicone (note 2)-treated titanated mica | 5.0 |
| 11. Alkylsilicone branched silicone (note 2)-treated sericite | 11.5 |

(note 1) Crosslinked dimethylpolysiloxane: KSG-16 (manufactured by Shin-Etsu Chemical Co., Ltd.)
(note 2) Alkylsilicone branched silicone: KF-9909 (manufactured by Shin-Etsu Chemical Co., Ltd.)

(Production Method)

A: Components 1 to 5 were mixed and heated to 80° C. to achieve a uniform dispersion.

B: Components 6 to 11 were added to the mixture obtained in A, and the resulting mixture was heated to 80° C. to obtain a uniform dispersion.

C: The mixture obtained in B was cooled to room temperature, yielding a cheek colorant.

The cheek colorant obtained in this manner was sponge-like, was readily picked up, exhibited good spreadability, and displayed favorable feelings upon use, with no greasiness or powderiness. Further, the water resistance, water repellency and sweat resistance were favorable, retention was good, and the colorant was resistant to cosmetic breakdown and exhibited excellent stability, with no change upon temperature variation and no change over time.

Example 39

Eye Colorant

| Components | mass (%) |
|---|---|
| 1. Isotridecyl isononanoate | 20.0 |
| 2. Squalane | 20.0 |
| 3. Silicone microparticles-1 | 6.0 |
| 4. Dextrin palmitate | 10.0 |
| 5. Crosslinked dimethylpolysiloxane (note 1) | 12.0 |
| 6. Barium sulfate | 5.0 |
| 7. Polyethylene terephthalate/Al powder | 4.5 |
| 8. Alkylsilicone branched silicone (note 2)-treated titanated mica | 13.5 |
| 9. Tocopherol | appropriate amount |

-continued

| Components | mass (%) |
|---|---|
| 10. Cosmetic glass flakes powder (note 3) | 1.5 |
| 11. Cosmetic iron oxide-coated glass flakes powder (note 4) | 7.5 |

(note 1) Crosslinked dimethylpolysiloxane: KSG-16 (manufactured by Shin-Etsu Chemical Co., Ltd.)
(note 2) Alkylsilicone branched silicone: KF-9909 (manufactured by Shin-Etsu Chemical Co., Ltd.)
(note 3) Cosmetic glass flakes powder: Glass flakes (manufactured by NSG Group)
(note 4) Cosmetic iron oxide-coated glass flakes powder: Metashine (manufactured by NSG Group)

(Production Method)
A: Components 1 to 5 were mixed and heated to 90° C. to achieve a uniform dispersion.
B: Components 6 to 11 were added to the mixture obtained in A, and the resulting mixture was heated to 90° C. to obtain a uniform dispersion.
C: The mixture obtained in B was cooled to room temperature, yielding an eye colorant.

The eye colorant obtained in this manner was jelly-like, was readily picked up, exhibited good spreadability, and displayed favorable feelings upon use, with no greasiness or powderiness. Further, the water resistance, water repellency and sweat resistance were favorable, retention was good, and the colorant was resistant to cosmetic breakdown and exhibited excellent stability, with no change upon temperature variation and no change over time.

Example 40

Foundation

| Components | mass (%) |
|---|---|
| 1. Dimethylpolysiloxane (viscosity: 6 mm²/s) | 23.0 |
| 2. Organic silicone resin (note 1) | 10.0 |
| 3. Alkylsilicone branched-crosslinked dimethylpolysiloxane (note 2) | 30.0 |
| 4. Silicone microparticles-1 | 8.0 |
| 5. Squalane | 1.0 |
| 6. Jojoba oil | 1.0 |
| 7. Diphenylsiloxyphenyl trimethicone (note 3) | 1.0 |
| 8. PMMA spherical powder | 2.0 |
| 9. Alkylsilicone branched silicone (note 4)-treated iron oxide | appropriate amount |
| 10. Alkylsilicone branched silicone (note 4)-treated titanium oxide | 6.0 |
| 11. Aluminum stearate-treated titanium oxide microparticles | 10.0 |
| 12. Tocopherol | appropriate amount |
| 13. Alkylsilicone branched silicone (note 4)-treated talc | 3.0 |
| 14. Alkylsilicone branched silicone (note 4)-treated sericite | 5.0 |

(note 1) Organic silicone resin: KF-7312L (manufactured by Shin-Etsu Chemical Co., Ltd.)
(note 2) Alkylsilicone branched-crosslinked dimethylpolysiloxane: KSG-048Z (manufactured by Shin-Etsu Chemical Co., Ltd.)
(note 3) Diphenylsiloxyphenyl trimethicone: KF-56A (manufactured by Shin-Etsu Chemical Co., Ltd.)
(note 4) Alkylsilicone branched silicone: KF-9909 (manufactured by Shin-Etsu Chemical Co., Ltd.)

(Production Method)
A: A portion of component 1 and components 2 to 8 were mixed and dispersed uniformly.
B: Using components 9 to 14 and the remainder of component 1, a roll mill was used to foam a uniform dispersion.
C: The mixture obtained in B was dispersed uniformly within the mixture obtained in A to complete preparation of a foundation.

The foundation obtained in this manner was souffle-like, was readily picked up, exhibited good spreadability, and displayed favorable feelings upon use, with no greasiness or powderiness. Further, the water resistance, water repellency and sweat resistance were favorable, retention was good, and the foundation was resistant to cosmetic breakdown and exhibited excellent stability, with no change upon temperature variation and no change over time.

What is claimed is:

1. A cosmetic comprising silicone microparticles, wherein the silicone microparticles comprise 100 parts by mass of silicone elastomer spherical microparticles having a volume average particle diameter within a range from 0.1 to 100 μm, and 0.5 to 25 parts by mass of a polyorganosilsesquioxane that coats a surface of the silicone elastomer spherical microparticles, and
the silicone elastomer is capable of absorbing not less than 200 parts by mass of a polymethylsiloxane having a viscosity at 25° C. of not more than 10 mm²/s per 100 parts by mass of the silicone elastomer and the silicone elastomer is a cured product of a liquid silicone composition comprising components (A), (B), and (C) as follows:

(A)
(A1) an organopolysiloxane represented of an average composition formula (1) shown below:

$$R^1_a R^2_b SiO_{(4-a-b)/2} \quad (1)$$

wherein $R^1$ is an unsubstituted or substituted monovalent hydrocarbon group of 1 to 30 carbon atoms excluding aliphatic unsaturated groups, $R^2$ is a monovalent olefinic unsaturated group of 2 to 6 carbon atoms, and a and b are positive numbers that satisfy $0<a<3$, $0<b\leq 3$, and $0.1\leq a+b\leq 3$, provided that a proportion of monovalent hydrocarbon groups of 6 to 30 carbon atoms is less than 5 mol % of all $R^1$ groups, in which not less than 90 mol % of all siloxane units other than siloxane units at molecular terminals are dimethylsiloxane units represented by a formula: $-(CH_3)_2SiO-$, and having a molecular weight of not less than 5,000, having two monovalent olefinic unsaturated groups within each molecule, and having a monovalent olefinic unsaturated group content of not more than 0.04 mol/100 g, or (A2) an organopolysiloxane represented of the average composition formula (1), in which not less than 90 mol % of all siloxane units other than siloxane units at molecular terminals are dimethylsiloxane units of a formula: $-(CH_3)_2SiO-$, and having a molecular weight of not less than 5,000, having at least three monovalent olefinic unsaturated groups within each molecule, and having a monovalent olefinic unsaturated group content of not more than 0.06 mol/100 g, or a combination of component (A1) and component (A2), (B)
(B1) an organohydrogenpolysiloxane represented of an average composition formula (2) shown below:

$$R^3_c H_d SiO_{(4-c-d)/2} \quad (2)$$

wherein $R^3$ is an unsubstituted or substituted monovalent hydrocarbon group of 1 to 30 carbon atoms excluding aliphatic unsaturated groups, and c and d are positive numbers that satisfy $0<c<3$, $0<d\leq 3$, and $0.1\leq c+d\leq 3$, provided that a proportion of monovalent hydrocarbon groups of 6 to 30 carbon atoms is less than 5 mol % of all $R^3$ groups, in which not less than 90 mol % of all siloxane units other than siloxane units at molecular termi-nals are dimethylsiloxane units represented by a formula: —(CH$_3$)$_2$SiO—, and having a molecular weight of not less than 5,000, having two hydrogen atoms bonded to silicon atoms within each molecule, and having a silicon atom-bonded hydrogen atom content of not more than 0.04 mol/100 g, or (B2) an organohydrogenpolysiloxane represented of the average composition formula (2), in which not less than 90 mol % of all siloxane units other than siloxane units at molecular terminals are dimethylsiloxane units represented by a formula: —(CH$_3$)$_2$SiO—, and having a molecular weight of not less than 5,000, having at least three hydrogen atoms bonded to silicon atoms within each molecule, and having a silicon atom-bonded hydrogen atom content of not more than 0.06 mol/100 g, or a combination of component (B1) and component (B2), (C) a platinum group metal-based catalyst, provided that when component (A) is component (A1), component (B) is either component (B2) or a combination of component (B1) and component (B2) and that components (A) and (B) are present in an amount that yields from 0.5 to 2 hydrogen atoms bonded to silicon atoms within component (B) per monovalent olefinic unsaturated group within component (A).

2. The cosmetic according to claim 1, wherein the silicone microparticles are obtained by a production method comprising:

hydrolyzing and condensing an organotrialkoxysilane in a water medium, in the presence of an alkaline material and silicone elastomer spherical microparticles having a volume average particle diameter within a range from 0.1 to 100 μm, thereby coating a surface of the silicone elastomer spherical microparticles with a polyorganosilsesquioxane, wherein the silicone elastomer is capable of absorbing not less than 200 parts by mass of a polymethylsiloxane having a viscosity at 25° C. of not more than 10 mm$^2$/s per 100 parts by mass of the silicone elastomer.

3. The cosmetic according to claim 1, further comprising a silicone-based oily component.

4. The cosmetic according to claim 3, wherein the silicone microparticles and the silicone-based oily component are included as an oily gel composition that comprises the silicone microparticles and the silicone-based oily component.

5. The cosmetic according to claim 4, further comprising a cosmetically acceptable carrier, wherein the oily gel composition is mixed with the carrier.

* * * * *